(12) United States Patent
Caplan et al.

(10) Patent No.: US 6,201,640 B1
(45) Date of Patent: Mar. 13, 2001

(54) MAGNIFICATION VIEWER

(75) Inventors: Charles Howard Caplan, Middleton, WI (US); Richard Alfred Buchroeder, Tucson, AZ (US); Frederick Nicholas Bushroe, Tucson, AZ (US); Anthony Ralph Ford, Tucson, AZ (US)

(73) Assignee: Surgical Acuity, Inc

( * ) Notice: Subject to any disclaimer, the term of this patent is extended or adjusted under 35 U.S.C. 154(b) by 0 days.

(21) Appl. No.: 09/062,936

(22) Filed: Apr. 20, 1998

Related U.S. Application Data

(60) Provisional application No. 60/069,496, filed on Dec. 15, 1997.

(51) Int. Cl.⁷ ............................. G02B 23/00; G02B 27/02
(52) U.S. Cl. .......................... 359/418; 359/362; 359/480; 351/158
(58) Field of Search .................... 359/362, 399, 359/407, 425–429, 432, 811, 816, 900, 744, 645, 694–700; 351/158, 41–45

(56) References Cited

U.S. PATENT DOCUMENTS

| | | | |
|---|---|---|---|
| 1,159,233 | * 11/1915 | Konig | 359/645 |
| 1,507,111 | * 9/1924 | Erfle | 359/744 |
| 1,688,113 | * 10/1928 | Bornkessel | 359/815 |
| 2,456,521 | * 12/1948 | Maxwell | 359/431 |
| 2,550,962 | * 5/1951 | Brandon | 359/425 |
| 2,986,969 | * 6/1961 | Muncheryan | 359/480 |
| 3,273,456 | * 9/1966 | Feinbloom | 351/158 |
| 3,865,468 | * 2/1975 | Holcomb | 359/815 |
| 3,877,793 | * 4/1975 | Nakagawa | 359/701 |
| 4,273,423 | * 6/1981 | Uesugi | 359/701 |
| 5,076,682 | * 12/1991 | Pasfield | 351/158 |
| 5,088,809 | * 2/1992 | Portney | 351/158 |
| 5,627,690 | * 5/1997 | Caplan et al. | 359/744 |
| 5,680,195 | * 10/1997 | Pekar et al. | 359/407 |

FOREIGN PATENT DOCUMENTS

1645925 * 4/1991 (RU) .................................. 359/407

\* cited by examiner

*Primary Examiner*—Thong Nguyen
(74) *Attorney, Agent, or Firm*—Sheridan Ross P.C.

(57) ABSTRACT

A housing for a magnification loupe is provided having a body portion for an eyepiece lens and a nose portion for an objective lens. The body portion for the eyepiece lens includes outer circumferential threads over which the objective nose portion fits. The objective nose portion includes a pin slot defining an arc across the body of the nose. The arc is configured such that a pin may be secured through the holes in the nose piece to co-act with the threads of the eyepiece body such that radial movement is prohibited.

5 Claims, 17 Drawing Sheets

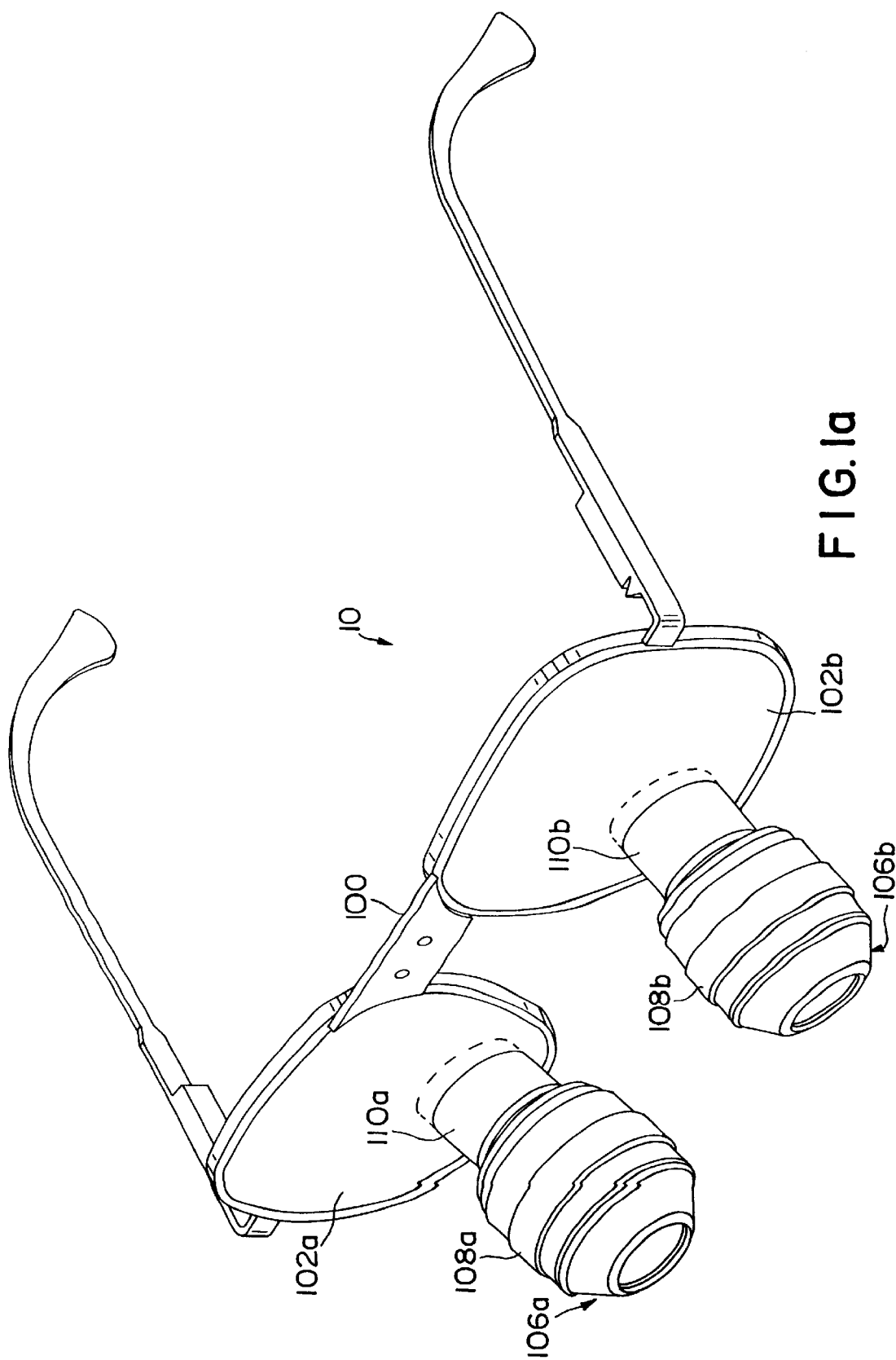

MAGNIFICATION VIEWER

CROSS-REFERENCE TO RELATED APPLICATION

This application is based on and claims priority of Provisional Application Serial No. 60/069,496, filed Dec. 15, 1997.

BACKGROUND OF TEE INVENTION

1. Field of the Invention

The present invention relates to magnification viewers worn by surgeons and dentists. In particular, the invention relates to an assembly for optical viewers or loupes which allow a user to adjust an objective lens at a predetermined distance from an eyepiece lens to vary the focal point.

2. Description of the Related Art

Magnification viewers generally including pairs of magnification loupes, are worn by dentists and surgeons for extended periods of time during clinical procedures, so as to provide clarity of view while avoiding a hunched-over position that can result in debilitating neck and back strain, which can have an adverse effect on the success of the operation. The viewers permit the clinician to operate at a greater working distance from the patient. Higher magnification viewers also reduce the clinician's exposure to aerosols. Because clinicians use magnification viewers during surgery and other procedures requiring manual precision, it is important that they be light-weight, comfortable and have good clarity and wide field of vision while providing high magnification and good depth of field.

Surgical telescopes may be attached to a spectacle frame in one of two manners: outside-the-carrier or prescription lens ("outside-the-lens"), on an adjustment mechanism that provides for adjustment of the interpupillary distance and convergent angle variability, or through-the-lens, permanently cemented and fixed in place. As noted above, magnification viewers used by surgeons and dentists typically have a predetermined magnification. Neither the working distance nor the magnification may be changed without a tedious process of replacing either individual lens elements or the entire optical loupes themselves. Accordingly, there is a need for a simple method for changing the magnification of viewers being worn by a surgeon or dentist, as well as for altering the working distance of viewers having a particular magnification.

SUMMARY OF THE INVENTION

In accordance with one embodiment of the invention, a housing for a magnification loupe is provided having an eyepiece portion for an eyepiece lens and a nose portion for an objective lens. The body portion for the eyepiece lens includes outer circumferential threads over which the objective nose portion fits to enable the distance between the lenses in the body and nose portions to be varied in order to vary the working distance of the loupe. The objective nose portion includes a pair of apertures for receiving a pin. The apertures are configured such that the pin forms a chord across the body of the nose portion and co-acts with the threads of the eyepiece body forming an axial mechanical stop to prevent the nose portion from being removed during adjustment.

Magnification loupes according to the present invention include a nose housing for an objective lens and a body housing for an eyepiece lens. The system is configured such that the magnification of the magnification loupe may be changed simply by removing the nose housing and replacing it with another. The working distance for a particular magnification level may be adjusted by threading or unthreading the nose housing.

BRIEF DESCRIPTION OF THE DRAWINGS

A better understanding of the present invention is obtained when the following detailed description is considered in conjunction with the following drawings in which:

FIGS. 1a–1c are perspective views of a magnification loupe in accordance with the present invention illustrating the connection of a pair of magnification loupes according to an embodiment of the present invention secured through the lenses of a pair of spectacles forming a magnification viewer in accordance with the present invention;

FIG. 3b is a side cross-sectional view of the magnification loupe of FIG. 3a;

DETAILED DESCRIPTION OF THE INVENTION

Figure 1B:
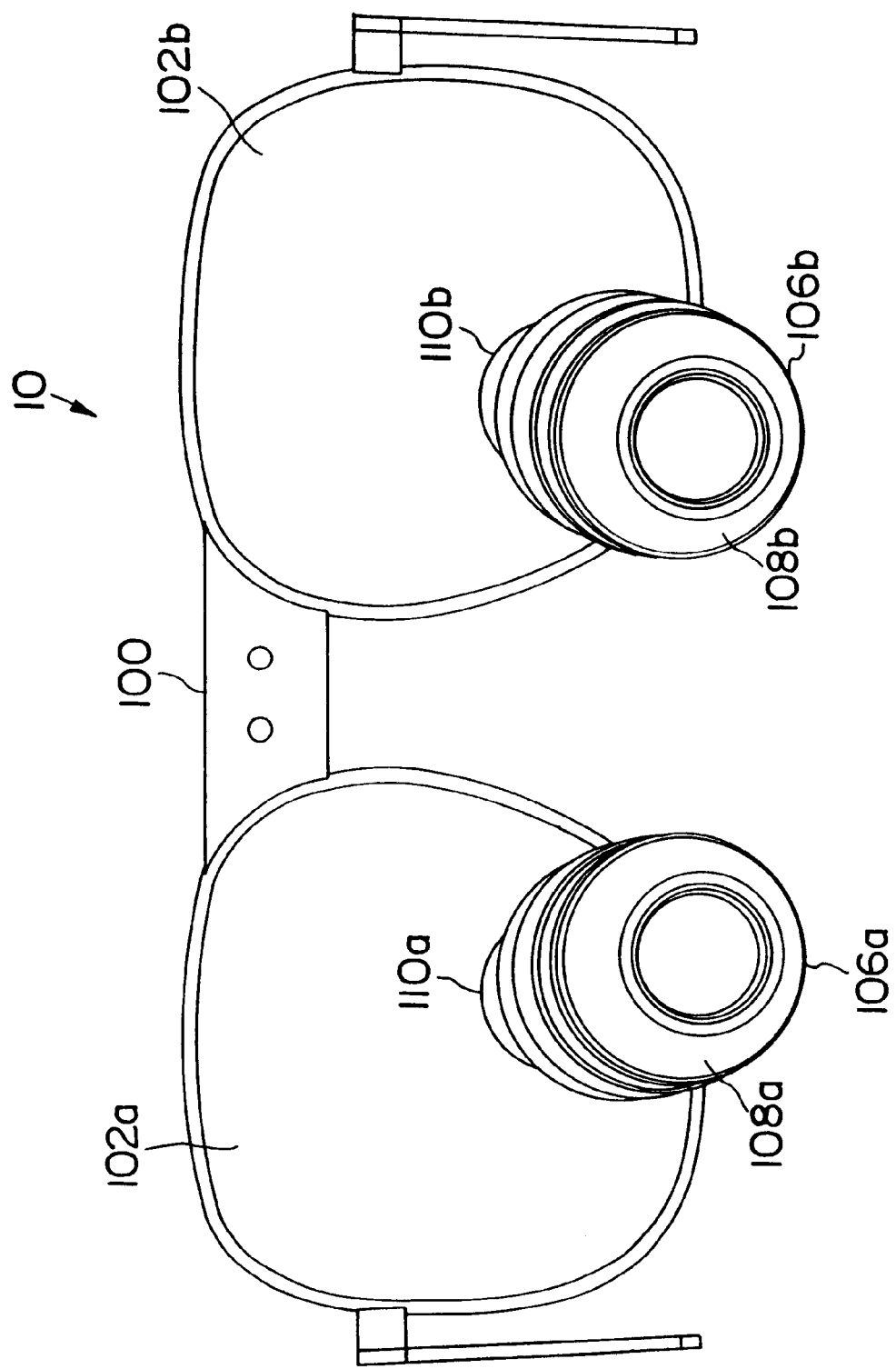

Turning now to the drawings and with particular attention to FIGS. 1a and 1b a magnification viewer 10 including a pair of spectacles 100 with through-the-lens magnification loupes 106a, 106b. As illustrated, the magnification loupes 106a, 106b are of the Keplerian design. The spectacles 100 include carrier lenses 102a, 102b. The carrier lenses 102a, 102b may be either plano lenses or prescription lenses. The magnification loupes 106a, 106b are fixed in the carrier lenses 102a, 102b to provide stereoscopic vision. The magnification loupes 106a, 106b are set at the user's interpupillary distance converging to a desired working distance, for example, anywhere from 12 to 24 or 13–21 inches. As will be discussed in greater detail below, from a selected working distance, the user has the option to vary the viewing distance by rotating the objective lens housing or nose housing 108a, 108b of each magnification loupe 106a, 106b to the desired focus. As will be discussed in more detail below, one of the objective lens housings 108a, 108b formed and the eyepiece housings 110a, 110b are formed with threads, which cooperate with a pin attached to the other housing to form a threaded coupling. The eyepiece housings, 110a, 110b, in turn, are secured to the carrier lenses 102a, 102b by various techniques, including a friction fit on with an adhesive, such as epoxy. Alternatively, the eyepiece housings 110a, 110b may be secured to the carrier lenses 102a, 102b by way of known threading on the outside of the eyepiece housings 110a, 110b matching threading on the carrier lenses 102a, 102b.

As will be discussed in greater detail below, magnifications of 3.3×, 3.8×, 4.3× and 4.8× are possible according to one embodiment of the invention to provide a wide range of selection. For each magnification, working distances of about 12", 16" and 24" may be provided. The carrier lenses 102a, 102b normally enable a user to focus comfortably at 500 mm, about −2D, a typical reading distance. The magnification loupes 106a, 106b, as will be discussed in greater detail below, further include a prism system (FIGS. 19–32). Each magnification loupe uses an identical prism and eyepiece lens system. For different magnifications, only the objective lenses are changed. The user may create depth of field by adjusting the focal distance of each eye depending upon the operation being performed. The focuses of each of the magnification loupes 106a, 106b may be changed independently. The aperture for the objective lens has been reduced in size to provide an increase in depth of field at high magnifications while still providing substantial light.

Figure 1C:
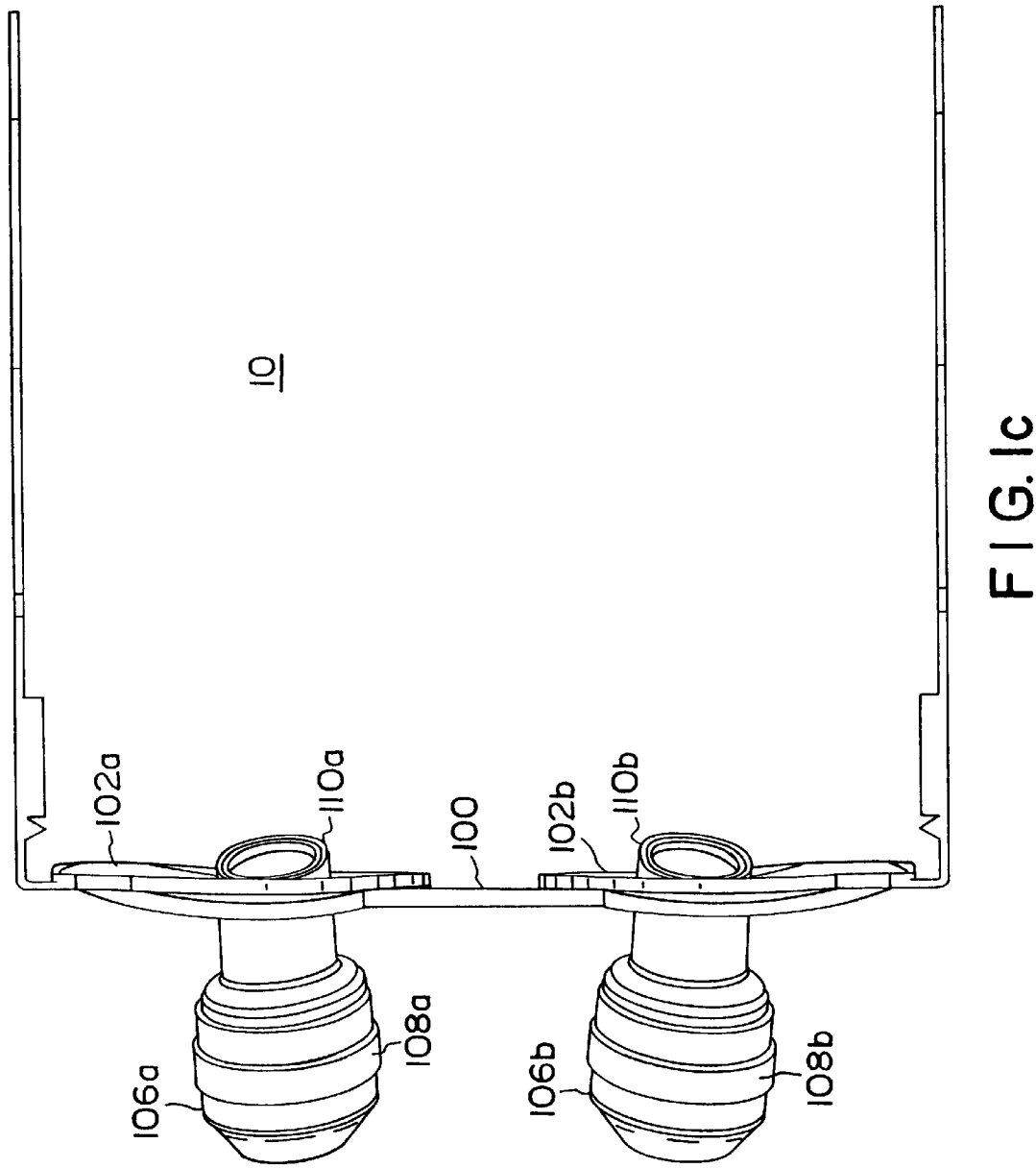
Figure 2:
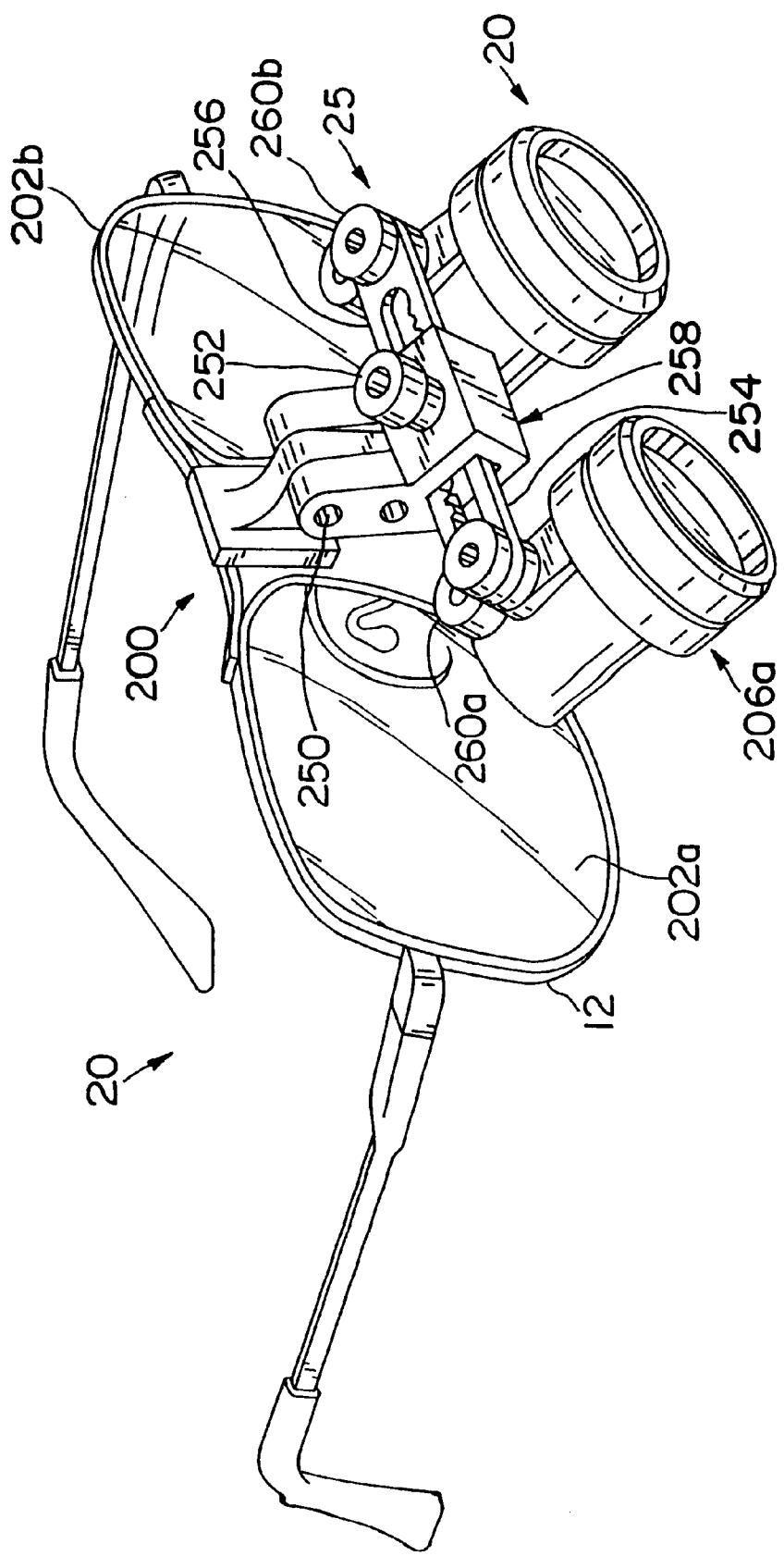
FIG. 2 is a perspective view of magnification loupes according to the present invention secured to an adjustable nose piece for securing to a pair of spectacles.

Turning now to FIG. 2, an alternative configuration of the magnification loupes 106a, 106b of FIGS. 1a and 1b is illustrated. It is noted that for the lens system 20 of FIG. 2, the optical configurations of the magnification loupes 206a, 206b are different from the through-the-lens configuration of FIG. 1, but the barrels or housings are similar in that only the objective lens need be changed to provide different magnifications. The prism and eyepiece remain the same. The optical system 20 of FIG. 2 includes a pair of spectacles 200 including a pair of carrier lenses 202a, 202b and a binocular magnification viewer 25, including a pair of magnification loupes 206a, 206b. As discussed in U.S. Pat. No. 5,667,291, the binocular magnification viewer 25 may be attached to the spectacles 200 by a pivot member 250. Alternatively, the magnification loupes 206a, 206b, may be mounted close to the spectacle lenses, for example, about 0.5 mm from the carrier lenses 202a, 202b. The pivot member 250 in turn, is attached to a bridge 258 which includes a bridge adjustment knob 252 for adjusting a pair of extension of arms 254, 256 to enable the interpupillary distances of the loupes 206a, 206b to be adjusted. The interpupillary distance of the magnification loupes 206a, 206b may further be adjusted by knobs 260a, 260b. The binocular magnification viewer 25 may be secured to the spectacles 200 by way of a clip, screws, glue or other known methods.

MECHANICAL CHARACTERISTICS

Figure 3A:
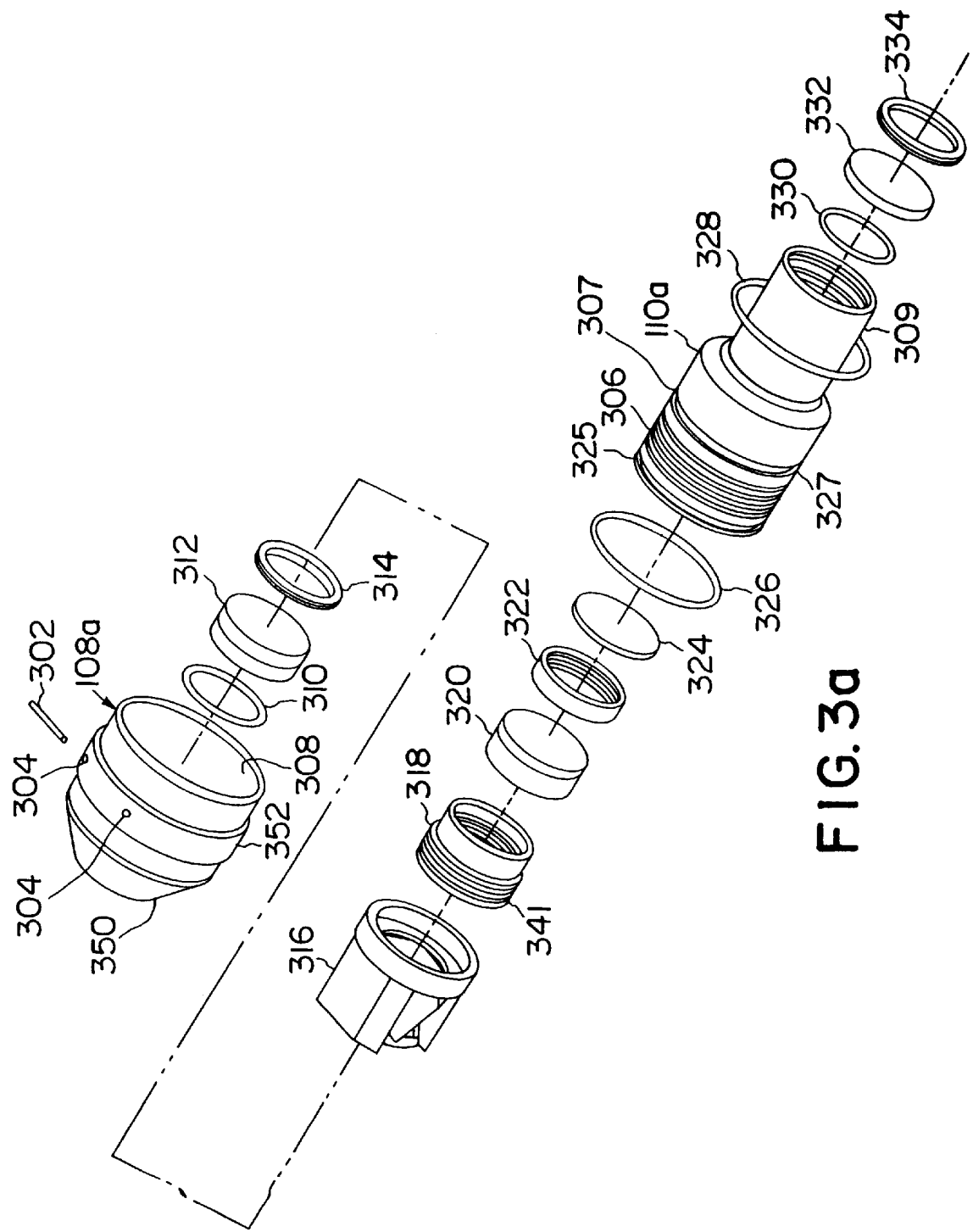
FIG. 3a is an exploded perspective view of the magnification loupe assembly for the magnification loupes of FIGS. 1 and 2.
Figure 3B:
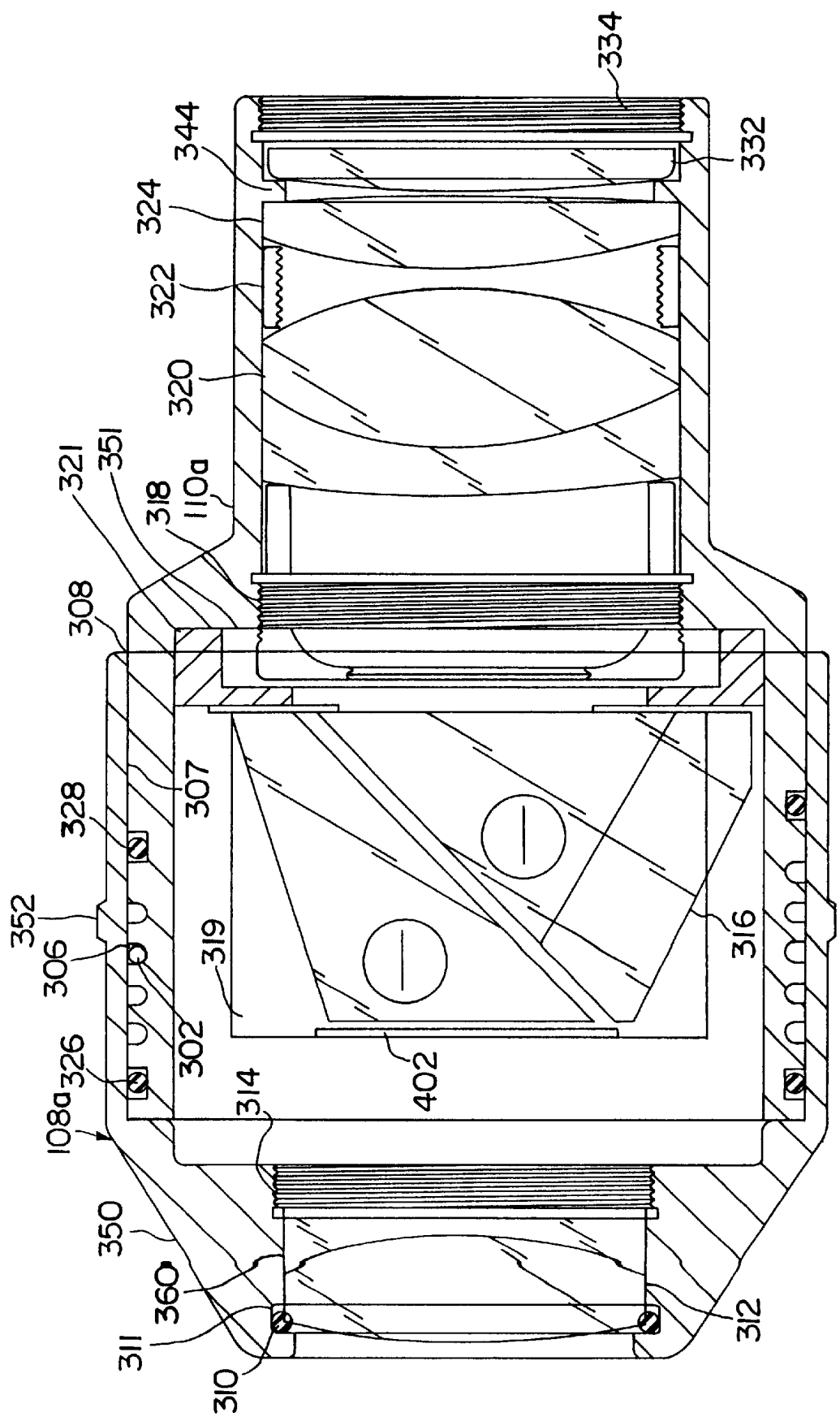

Turning now to FIG. 3a, an exploded perspective view of the magnification loupes 106 in accordance with the present invention are shown. The magnification loupes 106a, 106b include a nose or objective housing 108a and a body or eyepiece housing 110a. As illustrated, the objective housing 108a includes a frusto-conical front portion 350 and a generally cylindrical rear portion 352. It is noted that the housing 108 may be of different shapes; thus, FIG. 3 is exemplary only. The objective housing 108a includes a pair of apertures 304. The apertures 304 are configured to receive a pin 302 such that the pin 302 defines a chord across the cylindrical rear portion 352 of the objective housing 108a. More particularly with reference to FIG. 3B, the objective housing 108a includes an interior surface 308 which, engages an exterior surface 307 of the eyepiece housing 10a. Spiral threads 306 re formed into the surface of the eyepiece housing.111a. The apertures 304 are located in the objective housing 108a so that the pin 302 engage the spiral or threads 306. The pin 302 enables a threaded coupling between the two housing 108a and 108a even though only one housing 110a is formed with threads. The threaded coupling between the housings 106a and 108a permits the working distance of the loupes 106a, 106b to be adjusted by relating the objective housing 108a relative to the eyepiece housing 110a, which in turn, varies the distance between the eyepiece and objective lenses which varies the working distance of the loupes 106a, 106b.

Another important aspect of the invention, is that the configuration allows the magnification of the loupes 106a, 106b to be rather easily changed. More particularly, the pin 302 may be removably mounted relative to the objective housing 108a or fixedly mounted with the use of epoxy. Depending on the embodiment, the magnification of the loupe can be rather easily changed at the factory or by the user or both. In particular, as will be discussed in more detail below, the magnification of the loupe 106a, 106b is changed simply by changing the objective lens in the loupe 106a, 106b. The objective lenses are easily changed by removing the pin 302 which enables the objective housing 108a to be removed so that the objective lens 312 can be removed and replaced. As will be discussed in more detail below, an important aspect of the invention relates to the ability to vary the magnification of the loupe 106a, 106b.

As best illustrated in FIG. 3b, the objective lens 312 is configured to rest within a first interior portion 360 of the objective housing 108a. The interior portion 360 includes a circumferential slot 311 for seating an O-ring 310 therein. The objective lens 312 rests against the O-ring 310 and is engaged in place-by a threaded retainer ring 314. The retainer ring 314 includes external threads to engage corresponding threads on the interior portion 360 of the objective housing 108a.

Figure 4:
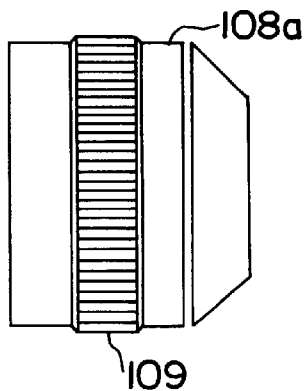
FIG. 4 is a side-elevation view of a nose housing forming a portion of the magnification viewers of FIGS. 1 and 2.
Figure 5A:
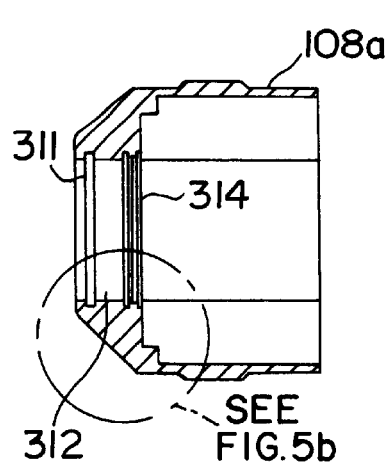
FIGS. 5a and 5b are side-cross-sectional views and detail side-cross-sectional views, respectively, of the housing of FIG. 4.
Figure 5B:
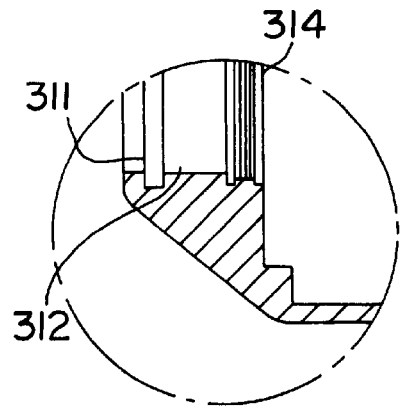
Figure 6:
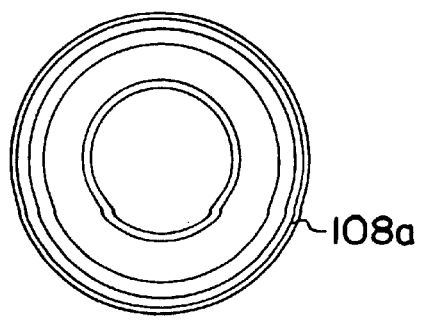
FIG. 6 is a top plan view of the nose housing of FIGS. 4 and 5.

Additional details concerning the objective housing 108a are illustrated in FIGS. 4–6. For example, the exterior of the objective housing 108a may include a knurled portion 109 for easy engagement of the objective housing 108a to the eyepiece housing 110a.

Figure 7:
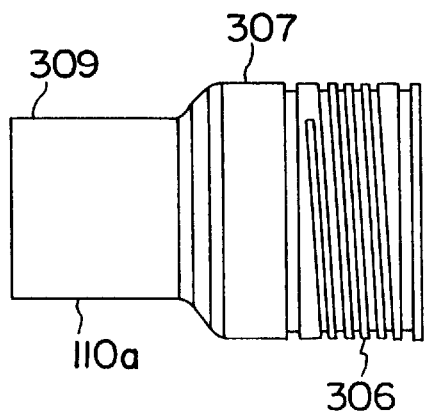
FIG. 7 is a side elevational view of the eyepiece housing of FIGS. 1 and 2.
Figure 8A:
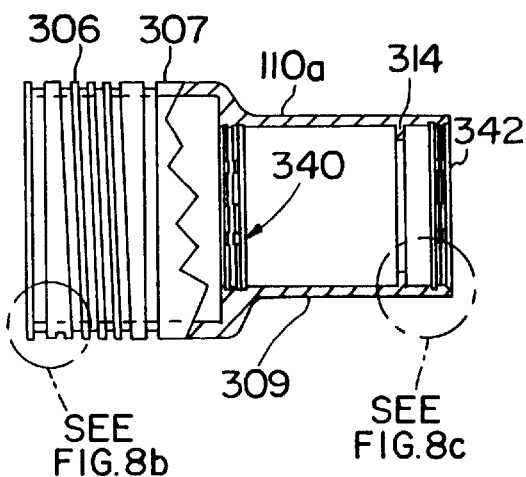
FIGS. 8a–8c are side cross-sectional views of the housing of FIG. 7, including details thereof.
Figure 8B:
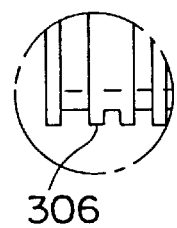
Figure 8C:
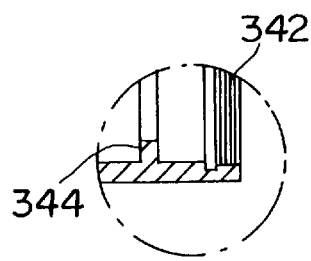
Figure 9:
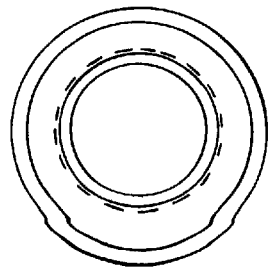
FIG. 9 is a top plan view of the eyepiece housing of FIGS. 7 and 8.

The eyepiece housing 110a, illustrated in greater detail in FIGS. 7–9, includes a forward engagement portion 307 and a rear cylindrical portion 309. As discussed above, the forward engagement portion 307 includes threads 306 for engagement with the pin 302. It is noted that according to one embodiment of the invention, the threads 306 are circular threads rather than notched or V-shaped threads so as to more effectively engage the pin 302. The eyepiece housing 110a includes internal threads 340 positioned where the engagement housing 307 meets the rear cylindrical portion 309. The threads 340 are configured to engage the threads 341 of the field stop 318 (FIGS. 3a, 3b). The rear cylindrical portion 309 of the eyepiece housing 110a further includes a circumferential platform 344, configured to receive a lens 332 for example, a prescription lens. The lens 332 is held in place against the platform 344 in contact with a prescription lens O-ring 330 and a retainer ring 334, which has external threads that engage the internal threads 342 of the eyepiece housing 110a. In the embodiment illustrated, the rear cylindrical portion 309 of the housing 110a is configured to be fastened to the carrier lens 102a by way of a suitable adhesive, such as epoxy. In an alternative embodiment, however, the rear cylindrical portion 309 may be provided with threads to engage similar threads in the carrier lens.

Figure 19A:
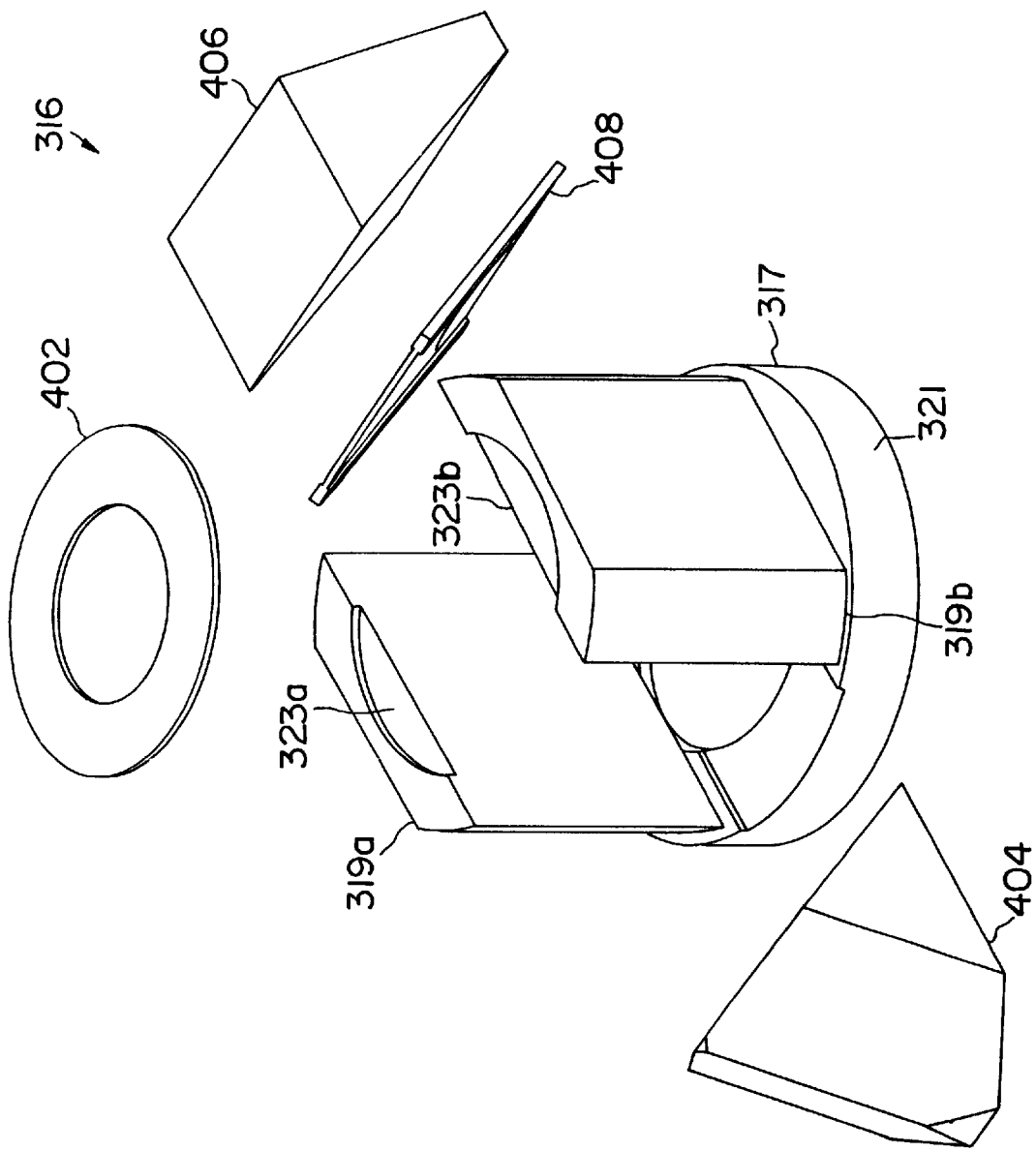
FIGS. 19a and 19b are exploded perspective views of a prism assembly for the magnification loupes of FIGS. 1a–3b.
Figure 19B:
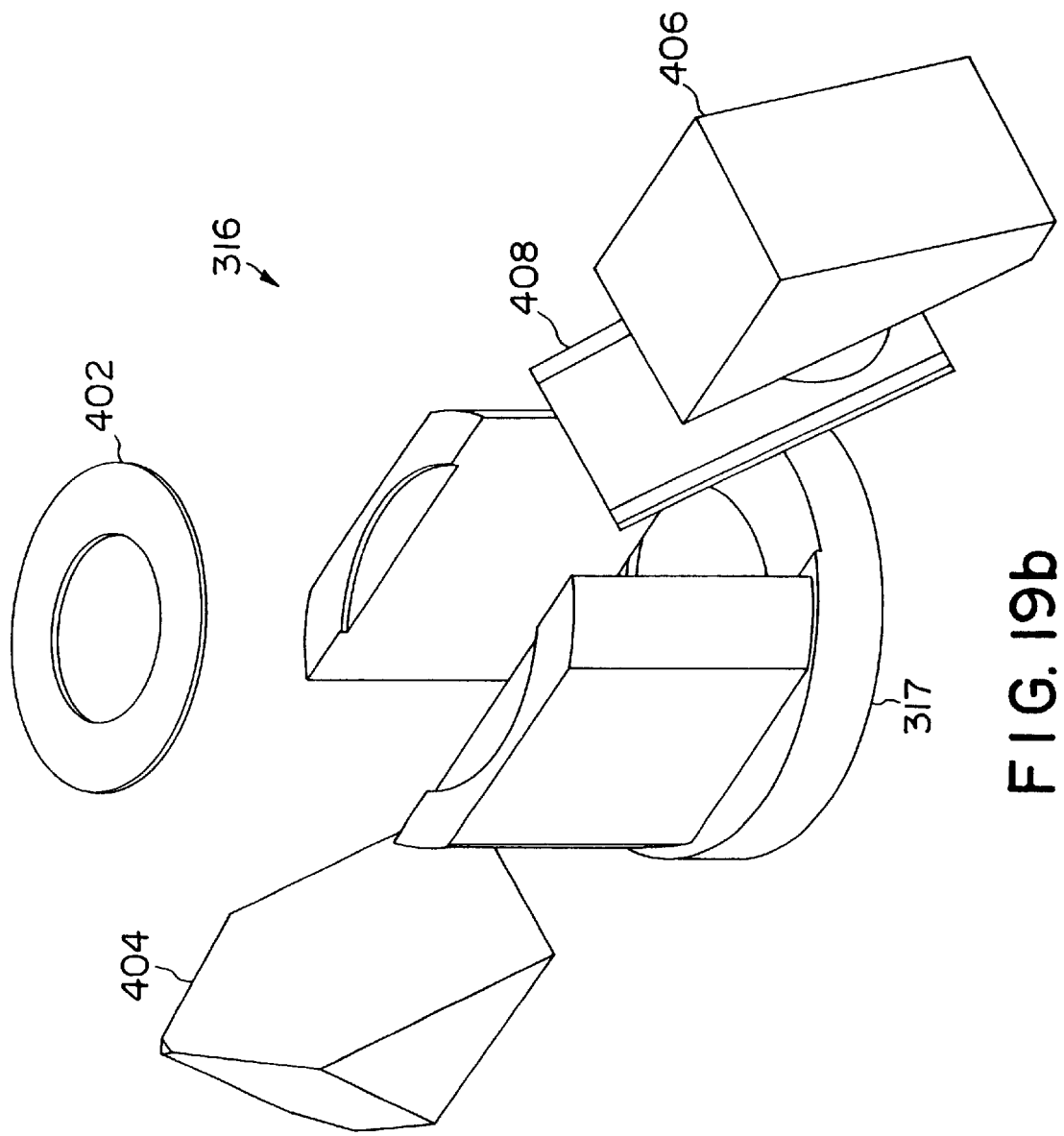
Figure 20A:
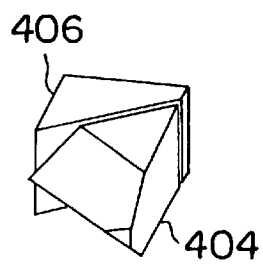
FIGS. 20a, 20b and 21–22 illustrate a prism for the prism assembly of FIGS. 19a and 19b.
Figure 20B:
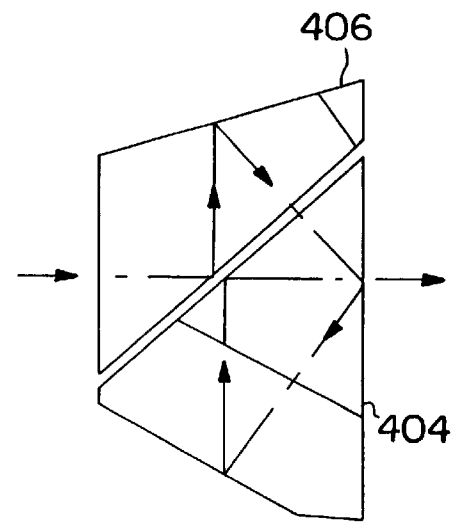
Figure 21:
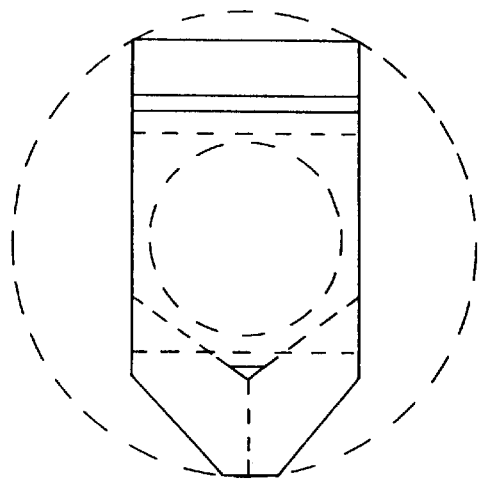
Figure 22:
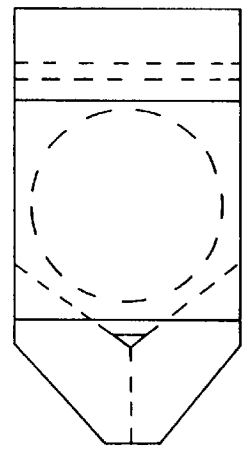
Figure 23:
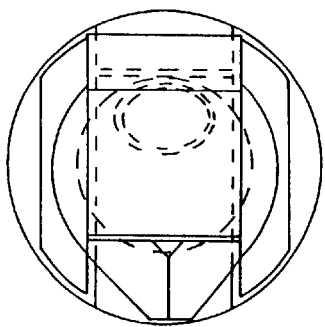
FIGS. 23–26 illustrate the prism assembly of, FIGS. 19a and 19b.
Figure 24:
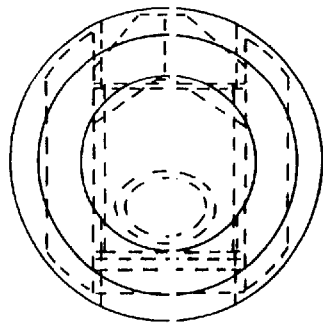
Figure 25:
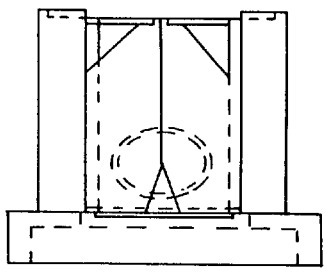
Figure 26:
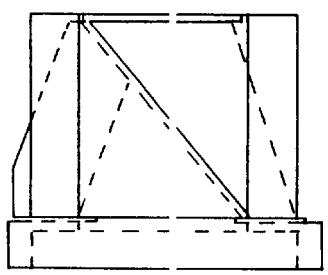
Figure 27:
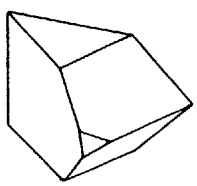
FIGS. 27–29 illustrate the roof prism of the prism assembly of FIGS. 19a and 19b.

The forward engagement portion 307 of the eyepiece housing 110a is further configured to receive a prism assembly 316 (FIGS. 19a, 19b). The prism assembly 316 includes a prism holder 317 including a pair of arms 319a, 319b, a base portion 321, and is adapted to fit within the housing 110a. The forward portions of the arms 319a, 319b include circular cutout portions 323a, 323b respectively, to engage a holder ring 402. The holder ring 402 is configured, when attached in place (such as by an adhesive), to secure the prism elements 404, 406, 408. According to one embodiment, the prism elements (FIGS. 20a–22) form a roof-pechan prism separated by a spacer 408. The spacer 408 is formed, for example, of a blackened ridge metal with a six millimeter diameter hole centered on the optical axis. The prism surfaces on opposite sides of the spacer are generally parallel. The individual elements of the roof pechan prism 404, 406 and 408 are illustrated in FIGS. 25–27 and 28–30, respectively. The prism elements are formed from Schott BAK4 or LAK10 glass.

Figure 10:
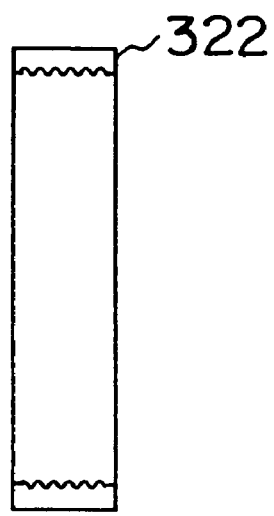
FIG. 10 is side elevational view of a spacer for the magnification loupes of FIGS. 1 and 2.
Figure 11:
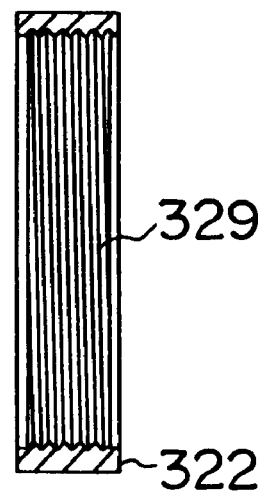
FIG. 11 is a side cross-sectional view of the spacer of FIG. 10.
Figure 12:
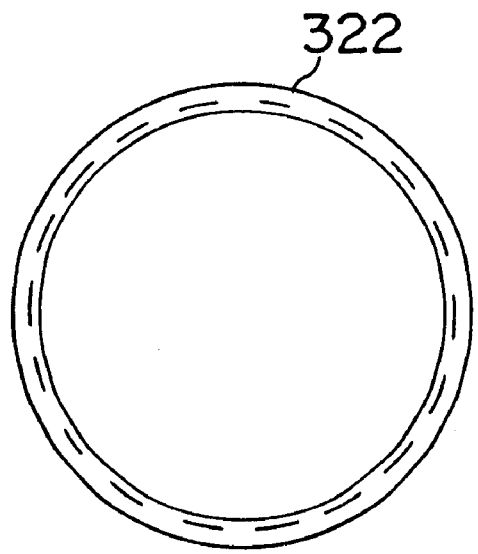
FIG. 12 is a top elevational view of the spacer of FIGS. 10 and 11.
Figure 13:
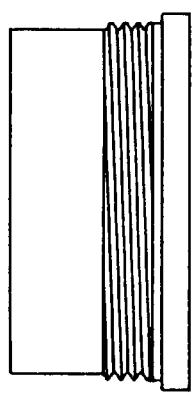
FIG. 13 is a side elevational view of a field stop of the magnification viewer of FIGS. 1a–3b.
Figure 14:
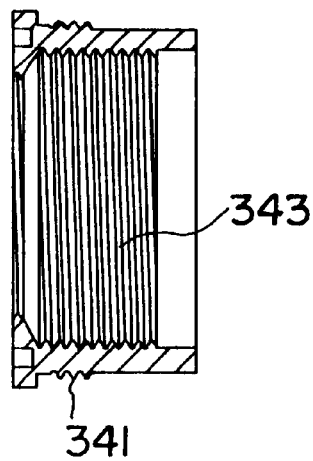
FIG. 14 is a side cross-sectional view of the field stop of FIG. 13.
Figure 15:
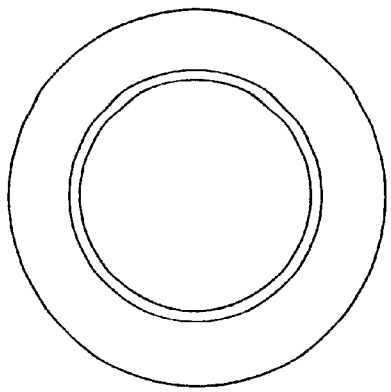
FIG. 15 is a top plan view of the field stop of FIGS. 13 and 14.
Figure 16:
FIG. 16 is a side elevational view of an objective lens retainer ring of the magnification loupes of FIGS. 1a–3b.
Figure 17:
FIG. 17 is side cross-sectional view of the objective retainer of FIG. 16.
Figure 18:
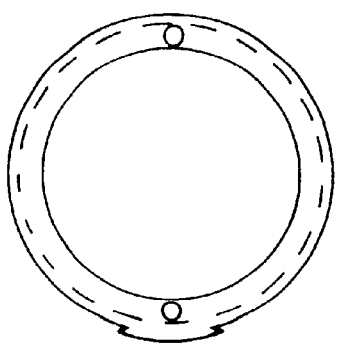
FIG. 18 is a top plan view of the objective retainer of FIGS. 16 and 17.

Turning back to FIGS. 3a –3b, the base of the prism assembly 316 is configured to rest against a rear wall 351 of the forward engagement portion 307 at approximately the position where it engages the rear cylindrical portion 309. A field stop 318 (FIGS. 13–15) having external threads 341 engages the corresponding internal threads 340 of the housing 110a. The field stop 318 further includes internal grooves 343. The rear cylindrical portion 309 of the housing 110a further houses the eyepiece lens elements. As shown, in FIG. 36 the eyepiece lens includes elements 320 and 324, separated by a spacer 322. The spacer 322 is illustrated in FIGS. 10–12 and may include internal concentric grooves 329 which form a light baffle. Finally, the eyepiece lens 324 rests against the platform 344.

As shown in FIGS. 3a and 3b, the exterior of the engagement housing 307 includes a pair of concentric circumferential grooves 325, 327 configured to receive the O-rings 326, 328 respectively. The O-rings 326, 328 additionally function to self-center the objective housing 108a and hence, the objective lens 312 relative to the eyepiece housing 110a.

While the configuration described and shown with regard to FIGS. 3a–3b relates to a through-the-lens viewer, a similar configuration may-be used in the outside-the-lens system shown in FIG. 2. Such a system may be used without a prescription lens and, as will be described in greater detail below, a different eyepiece system.

OPTICAL CHARACTERISTICS

Figure 28:
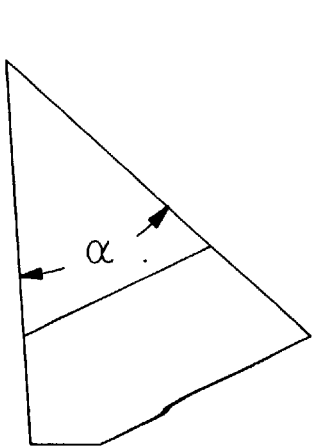
Figure 29:
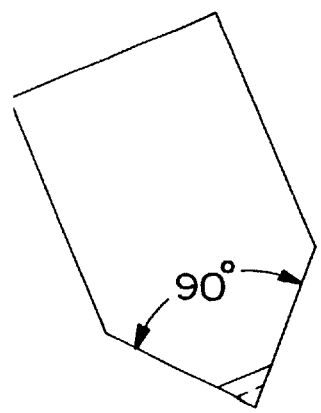
Figure 30:
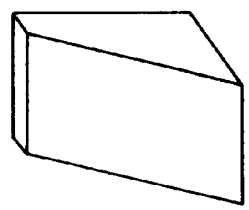
FIGS. 30–32 illustrate the second prism of the prism assembly of FIGS. 19a and 19b.
Figure 31:
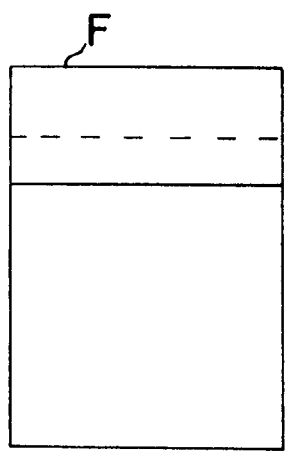
Figure 32:
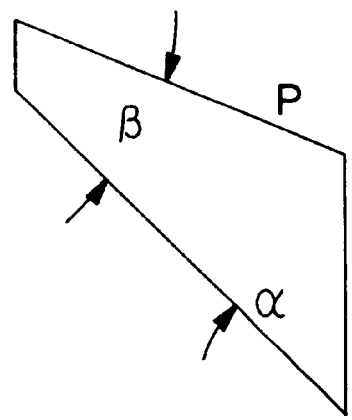
Figure 33:
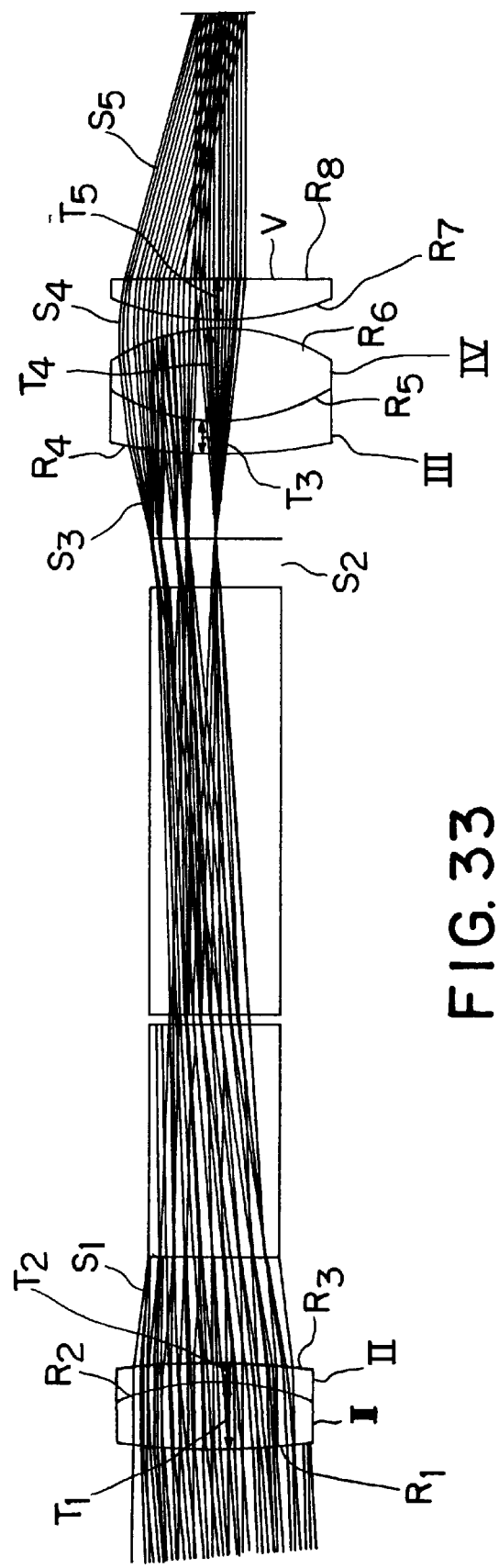
FIG. 33 is a diagram of the optical layout of the magnification loupe of FIGS. 1c, 3a and 3b.

Turning now to FIG. 33, a diagram illustrating the optical layout of the magnification loupe 106a, 106b of FIGS. 1a, 1b, 3a and 3b is shown. The magnification loupe 106a, 106b as illustrated in FIG. 33 includes a two-element objective lens including elements I-II and including a three-element eyepiece including elements III-V. R1, R2 etc., represent the radii of respective refractive surfaces; S1–S5 represent the thickness of the air spaces; and T1, T2, etc., represent the thicknesses of the lens elements. As discussed above, according to one embodiment of the invention, magnifications of 3.3×, 3.8×, 4.3× and 4.8× are provided. All magnifications use the same prism and eyepiece lens system. As shown in FIGS. 28 and 32, the prior angle α may be used in the range 45°–49°, preferably 48° to increase the optical performance of the device while the prism angle B (FIG. 32) may be selected to be 24°. Thus, a common eyepiece housing 110a and optical elements included therein may be used for all of the magnifications. As discussed above, only the objective lens needs to be changed in order to alter the magnification.

The user may create a depth of field by adjusting the focal distance of each eye differently depending on the operation being performed. For example, a heart surgeon may wish to view the entire depth of the heart at high magnification previously unattainable in conventional magnification systems where depth of field is limited. This can be accomplished by adjusting the focus of the left eye one-inch beyond the right. When both eyes are then opened, the heart can be viewed in its entirety. However, a dentist may only require the depth of the coronal portion of the tooth to be in focus and thus, would only separate the focus by a millimeter or two. Alternatively, both magnification loupes can be precisely focused at the same distance for procedures requiring the highest resolution. The following exemplary fields of view may be provided:

93 mm@3.3×@16"WD 82 mm@3.3×@16"WD 72 mm@3.3×@16"WD 65 mm@3.3×@16"WD

Exemplary construction data for a magnification loupe built according to the embodiment shown in FIGS. 1a–3b are given in Tables I-XII. The radii, thickness, and separation dimensions are given in millimeters. Roman numerals identify the lens elements in their respective order from the objective side to the eyepiece side; nd represents the refractive index of each element; $v_d$ is the abbe dispersion number; R1, R1, etc., represent the radii of the respective refractive surfaces in order from the objective side to the eyepoint side; T1, T2, etc., represent the thicknesses of the lens elements from the objective side to the eyepoint side; S1, S2 represent the thicknesses of air spaces respectively from the objective side to the eyepoint side measured along the optical centerline. Again, it is noted that the prism/objective distance 51, can differ by about 2.5 mm if BAK4 glass is used, rather than LAK10, as in the tables.

Figure 34:
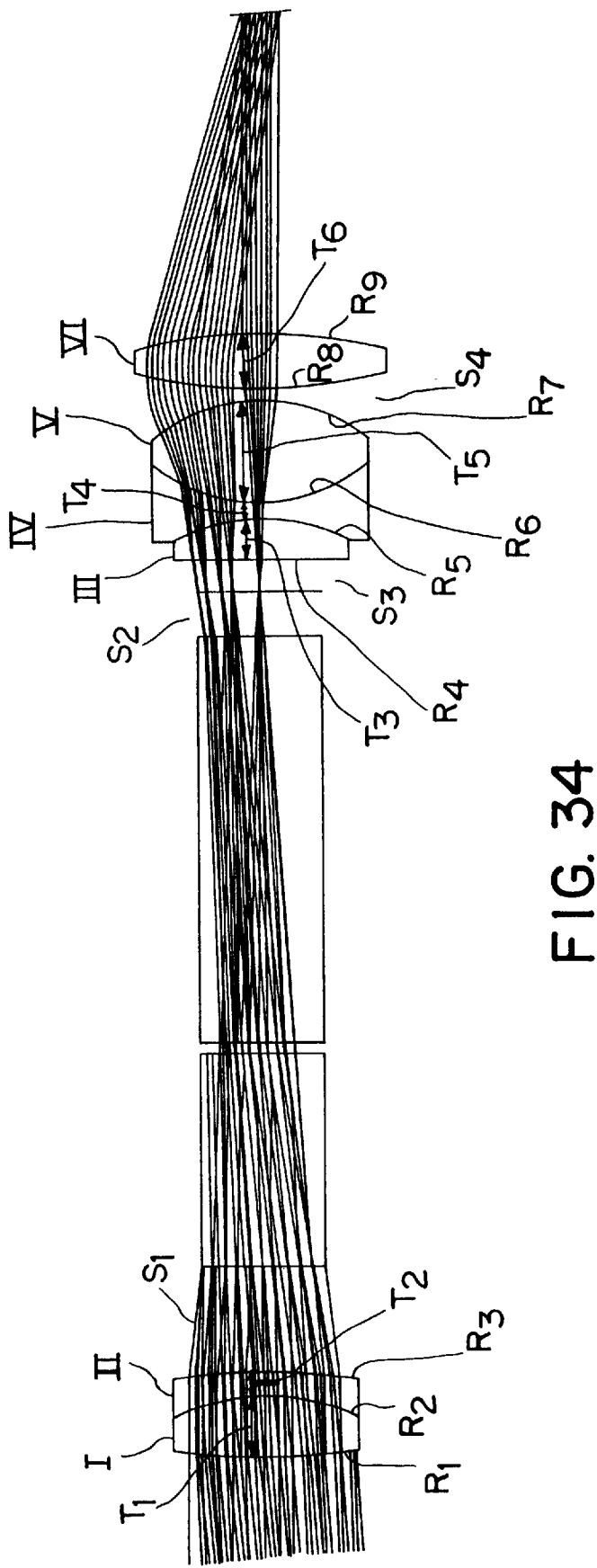
FIG. 34 is an optical layout diagram of the optical loupe of FIGS. 1a, 1b and 1c according to an alternate embodiment.

FIG. 34 illustrates an embodiment of the present invention having long eye relief characteristics. Again, the system shown in FIG. 34 employs the same prism and eyepieces, but separate objective doublets for each level of magnification. The objective doublets and the prism, however, are the same as for the through-the-lens embodiment shown in FIG. 33. Additionally, only the eyepiece lens is changed from the through-the-lens configuration. As compared the embodiment of FIG. 33, eye relief—the distance to exit pupil—has been improved from about 17.8 mm to about 22.8 mm.

In particular, the viewer according to FIG. 34 includes the two-element or doublet objective including elements I-II and a four-element eyepiece lens including elements III-VI. R1, R2 etc., again represent the radii of respective refractive surfaces; S1 and S2 represent the thicknesses of the air spaces; and T1, T2, etc., represent the thicknesses of the lens elements.

Exemplary construction data for loupes according to the embodiment of FIG. 34 are given in Tables XIII—XXIV.

TABLE I

3.3X (12" WD)

| Element | Glass | nd | vd | Radius | Thickness | Diameter | Sep. |
|---|---|---|---|---|---|---|---|
| I | Ohara BAH 27 | 1.7015 | 41.2 | $R_1 = 42.19$ | 3.5 | 13.4 | |
| II | Ohara PBH6W | 1.8052 | 25.4 | $R_2 = 12.45$<br>$R_3 = 36.00$ | 1.5 | 13.4 | |
| Prism A | BAK4<br>LAK10 | 1.5688<br>1.7200 | 56.13<br>50.41 | | | | $S_1 = 6.96$<br>$S_2 = 3.41$<br>$S_3 = 7.04$ |
| Prism B | BAK4<br>LAK10 | 1.5688<br>1.7200 | 56.13<br>50.41 | | | | $S_4 = 0.05$<br>$S_5 = 17.86$ |
| III | Ohara PBH6W | 1.8052 | 25.4 | $R_3 = 44.00$<br>$R_4 = 13.00$ | 2.0 | 15.4 | |
| IV | Ohara FSL5 | 1.4875 | 70.2 | $R_5 = 13.00$<br>$R_6 = 13.00$ | 6.5 | 15.4 | |
| V | Ohara BAH10 | 1.6700 | 47.3 | $R_7 = 15.59$<br>$R_8 = 94.04$ | 3.0 | 15.4 | |

TABLE II

3.3X (16" WD)

| Element | Glass | nd | vd | Radius | Thickness | Diameter | Sep. |
|---|---|---|---|---|---|---|---|
| I | Ohara BAH 27 | 1.7015 | 41.2 | $R_1 = 42.19$ | 3.5 | 13.4 | |
| II | Ohara PBH6W | 1.8052 | 25.4 | $R_2 = 12.45$<br>$R_3 = 36.00$ | 1.5 | 13.4 | |
| Prism A | BAK4<br>LAK10 | 1.5688<br>1.7200 | 56.13<br>50.41 | | | | $S_1 = 5.01$<br>$S_2 = 3.41$<br>$S_3 = 7.04$ |
| Prism B | BAK4<br>LAK10 | 1.5688<br>1.7200 | 56.13<br>50.41 | | | | $S_4 = 0.05$<br>$S_5 = 17.86$ |
| III | Ohara PBH6W | 1.8052 | 25.4 | $R_3 = 44.00$<br>$R_4 = 13.00$ | 2.0 | 15.4 | |
| IV | Ohara FSL5 | 1.4875 | 70.2 | $R_5 = 13.00$<br>$R_6 = 13.00$ | 6.5 | 15.4 | |
| V | Ohara BAH10 | 1.6700 | 47.3 | $R_7 = 15.59$<br>$R_8 = 94.04$ | 3.0 | 15.4 | |

TABLE III

3.3X (24" WD)

| Element | Glass | nd | vd | Radius | Thickness | Diameter | Sep. |
|---|---|---|---|---|---|---|---|
| I | Ohara BAH 27 | 1.7015 | 41.2 | $R_1 = 42.19$ | 3.5 | 13.4 | |
| II | Ohara PBH6W | 1.8052 | 25.4 | $R_2 = 12.45$<br>$R_3 = 36.00$ | 1.5 | 13.4 | |
| Prism A | BAK4<br>LAK10 | 1.5688<br>1.7200 | 56.13<br>50.41 | | | | $S_1 = 3.63$<br>$S_2 = 3.41$<br>$S_3 = 7.04$ |
| Prism B | BAK4<br>LAK10 | 1.5688<br>1.7200 | 56.13<br>50.41 | | | | $S_4 = 0.05$<br>$S_5 = 17.86$ |
| III | Ohara PBH6W | 1.8052 | 25.4 | $R_3 = 44.00$<br>$R_4 = 13.00$ | 2.0 | 15.4 | |
| IV | Ohara FSL5 | 1.4875 | 70.2 | $R_5 = 13.00$<br>$R_6 = 13.00$ | 6.5 | 15.4 | |
| V | Ohara BAH10 | 1.6700 | 47.3 | $R_7 = 15.59$<br>$R_8 = 94.04$ | 3.0 | 15.4 | |

TABLE IV 3.8X
(12" WD)

| Element | Glass | nd | vd | Radius | Thickness | Diameter | Sep. |
|---|---|---|---|---|---|---|---|
| I | Ohara BAH 27 | 1.7015 | 41.2 | $R_1 = 42.04$ $R_2 = 14.61$ | 4.0 | 13.4 | |
| II | Ohara PBH6W | 1.8052 | 25.4 | $R_2 = 14.61$ $R_3 = 36.00$ | 1.5 | 13.4 | |
| Prism A | BAK4 | 1.5688 | 56.13 | | | | $S_1 = 12.38$ |
|  | LAK10 | 1.7200 | 50.41 | | | | $S_2 = 3.41$ |
|  |  |  |  | | | | $S_3 = 7.04$ |
| Prism B | BAK4 | 1.5688 | 56.13 | | | | $S_4 = 0.05$ |
|  | LAK10 | 1.7200 | 50.41 | | | | $S_5 = 17.86$ |
| III | Ohara PBH6W | 1.8052 | 25.4 | $R_3 = 44.00$ $R_4 = 13.00$ | 2.0 | 15.4 | |
| IV | Ohara FSL5 | 1.4875 | 70.2 | $R_5 = 13.00$ $R_6 = 13.00$ | 6.5 | 15.4 | |
| V | Ohara BAH10 | 1.6700 | 47.3 | $R_7 = 15.59$ $R_8 = 94.04$ | 3.0 | 15.4 | |

TABLE V 3.8X
(16" WD)

| Element | Glass | nd | vd | Radius | Thickness | Diameter | Sep. |
|---|---|---|---|---|---|---|---|
| I | Ohara BAH 27 | 1.7015 | 41.2 | $R_1 = 42.19$ $R_2 = 14.61$ | 4.0 | 13.4 | |
| II | Ohara PBH6W | 1.8052 | 25.4 | $R_2 = 14.61$ $R_3 = 36.00$ | 1.5 | 13.4 | |
| Prism A | BAK4 | 1.5688 | 56.13 | | | | $S_1 = 9.92$ |
|  | LAK10 | 1.7200 | 50.41 | | | | $S_2 = 3.41$ |
|  |  |  |  | | | | $S_3 = 7.04$ |
| Prism B | BAK4 | 1.5688 | 56.13 | | | | $S_4 = 0.05$ |
|  | LAK10 | 1.7200 | 50.41 | | | | $S_5 = 17.86$ |
| III | Ohara PBH6W | 1.8052 | 25.4 | $R_3 = 44.00$ $R_4 = 13.00$ | 2.0 | 15.4 | |
| IV | Ohara FSL5 | 1.4875 | 70.2 | $R_5 = 13.00$ $R_6 = 13.00$ | 6.5 | 15.4 | |
| V | Ohara BAH10 | 1.6700 | 47.3 | $R_7 = 15.59$ $R_8 = 94.04$ | 3.0 | 15.4 | |

TABLE VI 3.8X
(24" WD)

| Element | Glass | nd | vd | Radius | Thickness | Diameter | Sep. |
|---|---|---|---|---|---|---|---|
| I | Ohara BAH 27 | 1.7015 | 41.2 | $R_1 = 42.04$ $R_2 = 14.61$ | 4.0 | 13.4 | |
| II | Ohara PBH6W | 1.8052 | 25.4 | $R_2 = 14.61$ $R_3 = 36.00$ | 1.5 | 13.4 | |
| Prism A | BAK4 | 1.5688 | 56.13 | | | | $S_1 = 8.02$ |
|  | LAK10 | 1.7200 | 50.41 | | | | $S_2 = 3.41$ |
|  |  |  |  | | | | $S_3 = 7.04$ |
| Prism B | BAK4 | 1.5688 | 56.13 | | | | $S_4 = 0.05$ |
|  | LAK10 | 1.7200 | 50.41 | | | | $S_5 = 17.86$ |
| III | Ohara PBH6W | 1.8052 | 25.4 | $R_3 = 44.00$ $R_4 = 13.00$ | 2.0 | 15.4 | |
| IV | Ohara FSL5 | 1.4875 | 70.2 | $R_5 = 13.00$ $R_6 = 13.00$ | 6.5 | 15.4 | |
| V | Ohara BAH10 | 1.6700 | 47.3 | $R_7 = 15.59$ $R_8 = 94.04$ | 3.0 | 15.4 | |

TABLE VII

4.3X
(12" WD)

| Element | Glass | nd | vd | Radius | Thickness | Diameter | Sep. |
|---|---|---|---|---|---|---|---|
| I | Ohara BAH 27 | 1.7015 | 41.2 | $R_1 = 50.15$<br>$R_2 = 16.00$ | 4.0 | 13.4 | |
| II | Ohara PBH6W | 1.8052 | 25.4 | $R_2 = 16.00$<br>$R_3 = 47.79$ | 1.5 | 13.4 | |
| Prism A | BAK4<br>LAK10 | 1.5688<br>1.7200 | 56.13<br>50.41 | | | | $S_1 = 18.07$<br>$S_2 = 3.41$<br>$S_3 = 7.04$ |
| Prism B | BAK4<br>LAK10 | 1.5688<br>1.7200 | 56.13<br>50.41 | | | | $S_4 = 0.05$<br>$S_5 = 17.86$ |
| III | Ohara PBH6W | 1.8052 | 25.4 | $R_3 = 44.00$<br>$R_4 = 13.00$ | 2.0 | 15.4 | |
| IV | Ohara FSL5 | 1.4875 | 70.2 | $R_5 = 13.00$<br>$R_6 = 13.00$ | 6.5 | 15.4 | |
| V | Ohara BAH10 | 1.6700 | 47.3 | $R_7 = 15.59$<br>$R_8 = 94.04$ | 3.0 | 15.4 | |

TABLE VIII

4.3X
(16" WD)

| Element | Glass | nd | vd | Radius | Thickness | Diameter | Sep. |
|---|---|---|---|---|---|---|---|
| I | Ohara BAH 27 | 1.7015 | 41.2 | $R_1 = 50.15$<br>$R_2 = 16.00$ | 4.0 | 13.4 | |
| II | Ohara PBH6W | 1.8052 | 25.4 | $R_2 = 16.00$<br>$R_3 = 47.79$ | 1.5 | 13.4 | |
| Prism A | BAK4<br>LAK10 | 1.5688<br>1.7200 | 56.13<br>50.41 | | | | $S_1 = 15.56$<br>$S_2 = 3.41$<br>$S_3 = 7.04$ |
| Prism B | BAK4<br>LAK10 | 1.5688<br>1.7200 | 56.13<br>50.41 | | | | $S_4 = 0.05$<br>$S_5 = 17.86$ |
| III | Ohara PBH6W | 1.8052 | 25.4 | $R_3 = 44.00$<br>$R_4 = 13.00$ | 2.0 | 15.4 | |
| IV | Ohara FSL5 | 1.4875 | 70.2 | $R_5 = 13.00$<br>$R_6 = 13.00$ | 6.5 | 15.4 | |
| V | Ohara BAH10 | 1.6700 | 47.3 | $R_7 = 15.59$<br>$R_8 = 94.04$ | 3.0 | 15.4 | |

TABLE IX

4.3X
(24" WD)

| Element | Glass | nd | vd | Radius | Thickness | Diameter | Sep. |
|---|---|---|---|---|---|---|---|
| I | Ohara BAH 27 | 1.7015 | 41.2 | $R_1 = 50.15$<br>$R_2 = 16.00$ | 4.0 | 13.4 | |
| II | Ohara PBH6W | 1.8052 | 25.4 | $R_2 = 16.00$<br>$R_3 = 47.79$ | 1.5 | 13.4 | |
| Prism A | BAK4<br>LAK10 | 1.5688<br>1.7200 | 56.13<br>50.41 | | | | $S_1 = 13.13$<br>$S_2 = 3.41$<br>$S_3 = 7.04$ |
| Prism B | BAK4<br>LAK10 | 1.5688<br>1.7200 | 56.13<br>50.41 | | | | $S_4 = 0.05$<br>$S_5 = 17.86$ |
| III | Ohara PBH6W | 1.8052 | 25.4 | $R_3 = 44.00$<br>$R_4 = 13.00$ | 2.0 | 15.4 | |
| IV | Ohara FSL5 | 1.4875 | 70.2 | $R_5 = 13.00$<br>$R_6 = 13.00$ | 6.5 | 15.4 | |

TABLE IX-continued

| | | | 4.3X | | | | |
| | | | (24" WD) | | | | |
| Element | Glass | nd | vd | Radius | Thickness | Diameter | Sep. |
|---|---|---|---|---|---|---|---|
| V | Ohara BAH10 | 1.6700 | 47.3 | $R_7 = 15.59$ $R_8 = 94.04$ | 3.0 | 15.4 | |

TABLE X

| | | | 4.8X | | | | |
| | | | (12" WD) | | | | |
| Element | Glass | nd | vd | Radius | Thickness | Diameter | Sep. |
|---|---|---|---|---|---|---|---|
| I | Ohara BAH 27 | 1.7015 | 41.2 | 61.12 | 4.0 | 13.4 | |
| II | Ohara SFL6 | 1.8052 | 25.4 | 16.98 | 1.5 | 13.4 | |
| Prism A | BAK4 LAK10 | 1.5688 1.7200 | 56.13 50.41 | | | | $S_1 = 25.16$ $S_2 = 3.41$ $S_3 = 7.04$ |
| Prism B | BAK4 LAK10 | 1.5688 1.7200 | 56.13 50.41 | | | | $S_4 = 0.05$ $S_5 = 17.86$ |
| III | Ohara PBH6W | 1.8052 | 25.4 | $R_3 = 44.00$ $R_4 = 13.00$ | 2.0 | 15.4 | |
| IV | Ohara FSL5 | 1.4875 | 70.2 | $R_5 = 13.00$ $R_6 = 13.00$ | 6.5 | 15.4 | |
| V | Ohara BAH10 | 1.6700 | 47.3 | $R_7 = 15.59$ $R_8 = 94.04$ | 3.0 | 15.4 | |

TABLE XI

| | | | 4.8X | | | | |
| | | | (16" WD) | | | | |
| Element | Glass | nd | vd | Radius | Thickness | Diameter | Sep. |
|---|---|---|---|---|---|---|---|
| I | Ohara BAH 27 | 1.7015 | 41.2 | 61.12 | 4.0 | 13.4 | |
| II | Ohara SFL6 | 1.8052 | 25.4 | 16.98 | 1.5 | 13.4 | |
| Prism A | BAK4 LAK10 | 1.5688 1.7200 | 56.13 50.41 | | | | $S_1 = 21.23$ $S_2 = 3.41$ $S_3 = 7.04$ |
| Prism B | BAK4 LAK10 | 1.5688 1.7200 | 56.13 50.41 | | | | $S_4 = 0.05$ $S_5 = 17.86$ |
| III | Ohara PBH6W | 1.8052 | 25.4 | $R_3 = 44.00$ $R_4 = 13.00$ | 2.0 | 15.4 | |
| IV | Ohara FSL5 | 1.4875 | 70.2 | $R_5 = 13.00$ $R_6 = 13.00$ | 6.5 | 15.4 | |
| V | Ohara BAH10 | 1.6700 | 47.3 | $R_7 = 15.59$ $R_8 = 94.04$ | 3.0 | 15.4 | |

TABLE XII

| | | | 4.8X | | | | |
| | | | (24" WD) | | | | |
| Element | Glass | nd | vd | Radius | Thickness | Diameter | Sep. |
|---|---|---|---|---|---|---|---|
| I | Ohara BAH 27 | 1.7015 | 41.2 | 61.12 | 4.0 | 13.4 | |
| II | Oshara | 1.8052 | 25.4 | 16.98 | 1.5 | 13.4 | |

TABLE XII-continued

4.8X
(24" WD)

| Element | Glass | nd | vd | Radius | Thickness | Diameter | Sep. |
|---|---|---|---|---|---|---|---|
| | SFL6 | | | | | | |
| Prism A | BAK4 | 1.5688 | 56.13 | | | | $S_1$ = 18.22 |
| | LAK10 | 1.7200 | 50.41 | | | | $S_2$ = 3.41 |
| | | | | | | | $S_3$ = 7.04 |
| Prism B | BAK4 | 1.5688 | 56.13 | | | | $S_4$ = 0.05 |
| | LAK10 | 1.7200 | 50.41 | | | | $S_5$ = 17.86 |
| III | Ohara | 1.8052 | 25.4 | $R_3$ = 44.00 | 2.0 | 15.4 | |
| | PBH6W | | | $R_4$ = 13.00 | | | |
| IV | Ohara | 1.4875 | 70.2 | $R_5$ = 13.00 | 6.5 | 15.4 | |
| | FSL5 | | | $R_6$ = 13.00 | | | |
| V | Ohara | 1.6700 | 47.3 | $R_7$ = 15.59 | 3.0 | 15.4 | |
| | BAH10 | | | $R_8$ = 94.04 | | | |

TABLE XIII

3.3X
(12" WD)

| Element | Glass | nd | vd | Radius | Thickness | Diameter | Sep. |
|---|---|---|---|---|---|---|---|
| I | Ohara | 1.7015 | 41.2 | $R_1$ = 42.19 | 3.5 | 13.4 | |
| | BAH 27 | | | $R_2$ = 12.45 | | | |
| II | Ohara | 1.8052 | 25.4 | $R_3$ = 12.45 | 1.5 | 13.4 | |
| | PBH6W | | | $R_3$ = 36.00 | | | |
| Prism A | BAK4 | 1.5688 | 56.13 | | | | $S_1$ = 6.96 |
| | LAK10 | 1.7200 | 50.41 | | | | $S_2$ = 3.41 |
| | | | | | | | $S_3$ = 2.33 |
| Prism B | BAK4 | 1.5688 | 56.13 | | | | $S_4$ = 0.5 |
| | LAK10 | 1.7200 | 50.41 | | | | $S_5$ = 22.8 |
| III | Ohara | 1.5410 | 47.2 | $R_4$ = PLANO | 3.0 | 12.0 | |
| | S-TIL2 | | | $R_5$ = 12.61 | | | |
| IV | Ohara | 1.923 | 21.3 | $R_5$ = 12.61 | 1.5 | 15.4 | |
| | PBH71 | | | $R_6$ = 12.61 | | | |
| V | SCHOTT | 1.5168 | 64.2 | $R_7$ = 10.06 | 7.1 | 15.4 | |
| | BK7 | | | $R_6$ = 12.61 | | | |
| VI | SCHOTT | 1.744 | 44.8 | $R_8$ = 25.11 | 4.7 | 17.5 | |
| | S-LAM2 | | | $R_9$ = 25.11 | | | |

TABLE XIV

3.3X
(16" WD)

| Element | Glass | nd | vd | Radius | Thickness | Diameter | Sep. |
|---|---|---|---|---|---|---|---|
| I | Ohara | 1.7015 | 41.2 | $R_1$ = 42.19 | 3.5 | 13.4 | |
| | BAH 27 | | | $R_2$ = 12.45 | | | |
| II | Ohara | 1.8052 | 25.4 | $R_2$ = 12.45 | 1.5 | 13.4 | |
| | PBH6W | | | $R_3$ = 36.00 | | | |
| Prism A | BAK4 | 1.5688 | 56.13 | | | | $S_1$ = 5.1 |
| | LAK10 | 1.7200 | 50.41 | | | | $S_2$ = 3.41 |
| | | | | | | | $S_3$ = 2.33 |
| Prism B | BAK4 | 1.5688 | 56.13 | | | | $S_4$ = .5 |
| | LAK10 | 1.7200 | 50.41 | | | | $S_5$ = 22.8 |
| III | Ohara | 1.5410 | 47.2 | $R_4$ = PLANO | 3.0 | 12.0 | |
| | S-TIL2 | | | $R_5$ = 12.61 | | | |
| IV | Ohara | 1.923 | 21.3 | $R_5$ = 12.61 | 1.5 | 15.4 | |
| | PBH71 | | | $R_6$ = 12.61 | | | |
| V | SCHOTT | 1.5168 | 64.2 | $R_7$ = 10.06 | 7.1 | 15.4 | |
| | BK7 | | | $R_6$ = 12.61 | | | |

TABLE XIV-continued

3.3X
(16" WD)

| Element | Glass | nd | vd | Radius | Thickness | Diameter | Sep. |
|---|---|---|---|---|---|---|---|
| VI | SCHOTT S-LAM2 | 1.744 | 44.8 | $R_8$ = 25.11<br>$R_9$ = 25.11 | 4.7 | 17.5 | |

TABLE XV

3.3X
(24" WD)

| Element | Glass | nd | vd | Radius | Thickness | Diameter | Sep. |
|---|---|---|---|---|---|---|---|
| I | Ohara BAH 27 | 1.7015 | 41.2 | $R_1$ = 42.19<br>$R_2$ = 12.45 | 3.5 | 13.4 | |
| II | Ohara PBH6W | 1.8052 | 25.4 | $R_2$ = 12.45<br>$R_3$ = 36.00 | 1.5 | 13.4 | |
| Prism A | BAK4<br>LAK10 | 1.5688<br>1.7200 | 56.13<br>50.41 | | | | $S_1$ = 3.63<br>$S_2$ = 3.41<br>$S_3$ = 2.33 |
| Prism B | BAK4<br>LAK10 | 1.5688<br>1.7200 | 56.13<br>50.41 | | | | $S_4$ = .5<br>$S_5$ = 22.8 |
| III | Ohara S-TIL2 | 1.5410 | 47.2 | $R_4$ = PLANO<br>$R_5$ = 12.61 | 3.0 | 12.0 | |
| IV | Ohara PBH71 | 1.923 | 21.3 | $R_5$ = 12.61<br>$R_6$ = 12.61 | 1.5 | 15.4 | |
| V | SCHOTT BK7 | 1.5168 | 64.2 | $R_7$ = 10.06<br>$R_6$ = 12.61 | 7.1 | 15.4 | |
| VI | SCHOTT S-LAM2 | 1.744 | 44.8 | $R_8$ = 25.11<br>$R_9$ = 25.11 | 4.7 | 17.5 | |

TABLE XVI

3.8X
(12" WD)

| Element | Glass | nd | vd | Radius | Thickness | Diameter | Sep. |
|---|---|---|---|---|---|---|---|
| I | Ohara BAH 27 | 1.7015 | 41.2 | $R_1$ = 42.19<br>$R_2$ = 12.45 | 3.5 | 13.4 | |
| II | Ohara PBH6W | 1.8052 | 25.4 | $R_2$ = 12.45<br>$R_3$ = 36.00 | 1.5 | 13.4 | |
| Prism A | BAK4<br>LAK10 | 1.5688<br>1.7200 | 56.13<br>50.41 | | | | $S_1$ = 12.38<br>$S_2$ = 3.41<br>$S_3$ = 2.33 |
| Prism B | BAK4<br>LAK10 | 1.5688<br>1.7200 | 56.13<br>50.41 | | | | $S_4$ = .5<br>$S_5$ = 22.8 |
| III | Ohara S-TIL2 | 1.5410 | 47.2 | $R_4$ = PLANO<br>$R_5$ = 12.61 | 3.0 | 12.0 | |
| IV | Ohara PBH71 | 1.923 | 21.3 | $R_5$ = 12.61<br>$R_6$ = 12.61 | 1.5 | 15.4 | |
| V | SCHOTT BK7 | 1.5168 | 64.2 | $R_7$ = 10.06<br>$R_6$ = 12.61 | 7.1 | 15.4 | |
| VI | SCHOTT S-LAM2 | 1.744 | 44.8 | $R_8$ = 25.11<br>$R_9$ = 25.11 | 4.7 | 17.5 | |

TABLE XVII

3.8X
(16" WD)

| Element | Glass | nd | vd | Radius | Thickness | Diameter | Sep. |
|---|---|---|---|---|---|---|---|
| I | Ohara BAH 27 | 1.7015 | 41.2 | $R_1$ = 42.19<br>$R_2$ = 12.45 | 3.5 | 13.4 | |
| II | Ohara PBH6W | 1.8052 | 25.4 | $R_2$ = 12.45<br>$R_3$ = 36.00 | 1.5 | 13.4 | |
| Prism A | BAK4<br>LAK10 | 1.5688<br>1.7200 | 56.13<br>50.41 | | | | $S_1$ = 9.92<br>$S_2$ = 3.41<br>$S_3$ = 2.33 |
| Prism B | BAK4<br>LAK10 | 1.5688<br>1.7200 | 56.13<br>50.41 | | | | $S_4$ = .5<br>$S_5$ = 22.8 |
| III | Ohara S-TIL2 | 1.5410 | 47.2 | $R_4$ = PLANO<br>$R_5$ = 12.61 | 3.0 | 12.0 | |
| IV | Ohara PBH71 | 1.923 | 21.3 | $R_5$ = 12.61<br>$R_6$ = 12.61 | 1.5 | 15.4 | |
| V | SCHOTT BK7 | 1.5168 | 64.2 | $R_7$ = 10.06<br>$R_6$ = 12.61 | 7.1 | 15.4 | |
| VI | SCHOTT S-LAM2 | 1.744 | 44.8 | $R_8$ = 25.11<br>$R_9$ = 25.11 | 4.7 | 17.5 | |

TABLE XVIII

3.8X
(24" WD)

| Element | Glass | nd | vd | Radius | Thickness | Diameter | Sep. |
|---|---|---|---|---|---|---|---|
| I | Ohara BAH 27 | 1.7015 | 41.2 | $R_1$ = 42.19<br>$R_2$ = 12.45 | 3.5 | 13.4 | |
| II | Ohara PBH6W | 1.8052 | 25.4 | $R_2$ = 12.45<br>$R_3$ = 36.00 | 1.5 | 13.4 | |
| Prism A | BAK4<br>LAK10 | 1.5688<br>1.7200 | 56.13<br>50.41 | | | | $S_1$ = 8.02<br>$S_2$ = 3.41<br>$S_3$ = 2.33 |
| Prism B | BAK4<br>LAK10 | 1.5688<br>1.7200 | 56.13<br>50.41 | | | | $S_4$ = .5<br>$S_5$ = 22.8 |
| III | Ohara S-TIL2 | 1.5410 | 47.2 | $R_4$ = PLANO<br>$R_5$ = 12.61 | 3.0 | 12.0 | |
| IV | Ohara PBH71 | 1.923 | 21.3 | $R_5$ = 12.61<br>$R_6$ = 12.61 | 1.5 | 15.4 | |
| V | SCHOTT BK7 | 1.5168 | 64.2 | $R_7$ = 10.06<br>$R_6$ = 12.61 | 7.1 | 15.4 | |
| VI | SCHOTT S-LAM2 | 1.744 | 44.8 | $R_8$ = 25.11<br>$R_9$ = 25.11 | 4.7 | 17.5 | |

TABLE XIX

4.3X
(12" WD)

| Element | Glass | nd | vd | Radius | Thickness | Diameter | Sep. |
|---|---|---|---|---|---|---|---|
| I | Ohara BAH 27 | 1.7015 | 41.2 | $R_1$ = 42.19<br>$R_2$ = 12.45 | 3.5 | 13.4 | |
| II | Ohara PBH6W | 1.8052 | 25.4 | $R_2$ = 12.45<br>$R_3$ = 36.00 | 1.5 | 13.4 | |
| Prism A | BAK4<br>LAK10 | 1.5688<br>1.7200 | 56.13<br>50.41 | | | | $S_1$ = 18.7<br>$S_2$ = 3.41<br>$S_3$ = 2.33 |
| Prism B | BAK4<br>LAK10 | 1.5688<br>1.7200 | 56.13<br>50.41 | | | | $S_4$ = .5<br>$S_5$ = 22.8 |
| III | Ohara S-TIL2 | 1.5410 | 47.2 | $R_4$ = PLANO<br>$R_5$ = 12.61 | 3.0 | 12.0 | |
| IV | Ohara | 1.923 | 21.3 | $R_5$ = 12.61 | 1.5 | 15.4 | |

TABLE XIX-continued 4.3X
(12" WD)

| Element | Glass | nd | vd | Radius | Thickness | Diameter | Sep. |
|---|---|---|---|---|---|---|---|
| V | SCHOTT BK7 | 1.5168 | 64.2 | $R_6$ = 12.61<br>$R_7$ = 10.06<br>$R_6$ = 12.61 | 7.1 | 15.4 | |
| VI | SCHOTT S-LAM2 | 1.744 | 44.8 | $R_8$ = 25.11<br>$R_9$ = 25.11 | 4.7 | 17.5 | |

TABLE XX 4.3X
(16" WD)

| Element | Glass | nd | vd | Radius | Thickness | Diameter | Sep. |
|---|---|---|---|---|---|---|---|
| I | Ohara BAH 27 | 1.7015 | 41.2 | $R_1$ = 42.19<br>$R_2$ = 12.45 | 3.5 | 13.4 | |
| II | Ohara PBH6W | 1.8052 | 25.4 | $R_2$ = 12.45<br>$R_3$ = 36.00 | 1.5 | 13.4 | |
| Prism A | BAK4<br>LAK10 | 1.5688<br>1.7200 | 56.13<br>50.41 | | | | $S_1$ = 15.56<br>$S_2$ = 3.41<br>$S_3$ = 2.33 |
| Prism B | BAK4<br>LAK10 | 1.5688<br>1.7200 | 56.13<br>50.41 | | | | $S_4$ = .5<br>$S_5$ = 22.8 |
| III | Ohara S-TIL2 | 1.5410 | 47.2 | $R_4$ = PLANO<br>$R_5$ = 12.61 | 3.0 | 12.0 | |
| IV | Ohara PBH71 | 1.923 | 21.3 | $R_5$ = 12.61<br>$R_6$ = 12.61 | 1.5 | 15.4 | |
| V | SCHOTT BK7 | 1.5168 | 64.2 | $R_7$ = 10.06<br>$R_6$ = 12.61 | 7.1 | 15.4 | |
| VI | SCHOTT S-LAM2 | 1.744 | 44.8 | $R_8$ = 25.11<br>$R_9$ = 25.11 | 4.7 | 17.5 | |

TABLE XXI 4.3X
(24" WD)

| Element | Glass | nd | vd | Radius | Thickness | Diameter | Sep. |
|---|---|---|---|---|---|---|---|
| I | Ohara BAH 27 | 1.7015 | 41.2 | $R_1$ = 42.19<br>$R_2$ = 12.45 | 3.5 | 13.4 | |
| II | Ohara PBH6W | 1.8052 | 25.4 | $R_2$ = 12.45<br>$R_3$ = 36.00 | 1.5 | 13.4 | |
| Prism A | BAK4<br>LAK10 | 1.5688<br>1.7200 | 56.13<br>50.41 | | | | $S_1$ = 13.13<br>$S_2$ = 3.41<br>$S_3$ = 2.33 |
| Prism B | BAK4<br>LAK10 | 1.5688<br>1.7200 | 56.13<br>50.41 | | | | $S_4$ = .5<br>$S_5$ 22.8 |
| III | Ohara S-TIL2 | 1.5410 | 47.2 | $R_4$ = PLANO<br>$R_5$ = 12.61 | 3.0 | 12.0 | |
| IV | Ohara PBH71 | 1.923 | 21.3 | $R_5$ = 12.61<br>$R_6$ = 12.61 | 1.5 | 15.4 | |
| V | SCHOTT BK7 | 1.5168 | 64.2 | $R_7$ = 10.06<br>$R_6$ = 12.61 | 7.1 | 15.4 | |
| VI | SCHOTT S-LAM2 | 1.744 | 44.8 | $R_8$ = 25.11<br>$R_9$ = 25.11 | 4.7 | 17.5 | |

TABLE XXII 4.8X
(12" WD)

| Element | Glass | nd | vd | Radius | Thickness | Diameter | Sep. |
|---|---|---|---|---|---|---|---|
| I | Ohara BAH 27 | 1.7015 | 41.2 | $R_1$ = 42.19<br>$R_2$ = 12.45 | 3.5 | 13.4 | |
| II | Ohara PBH6W | 1.8052 | 25.4 | $R_2$ = 12.45<br>$R_3$ = 36.00 | 1.5 | 13.4 | |
| Prism A | BAK4<br>LAK10 | 1.5688<br>1.7200 | 56.13<br>50.41 | | | | $S_1$ = 25.16<br>$S_2$ = 3.41<br>$S_3$ = 2.33 |
| Prism B | BAK4<br>LAK10 | 1.5688<br>1.7200 | 56.13<br>50.41 | | | | $S_4$ = .5<br>$S_5$ = 22.8 |
| III | Ohara S-TIL2 | 1.5410 | 47.2 | $R_4$ = PLANO<br>$R_5$ = 12.61 | 3.0 | 12.0 | |
| IV | Ohara PBH71 | 1.923 | 21.3 | $R_5$ = 12.61<br>$R_6$ = 12.61 | 1.5 | 15.4 | |
| V | SCHOTT BK7 | 1.5168 | 64.2 | $R_7$ = 10.06<br>$R_6$ = 12.61 | 7.1 | 15.4 | |
| VI | SCHOTT S-LAM2 | 1.744 | 44.8 | $R_8$ = 25.11<br>$R_9$ = 25.11 | 4.7 | 17.5 | |

TABLE XXIII 4.8X
(16" WD)

| Element | Glass | nd | vd | Radius | Thickness | Diameter | Sep. |
|---|---|---|---|---|---|---|---|
| I | Ohara BAH 27 | 1.7015 | 41.2 | $R_1$ = 42.19<br>$R_2$ = 12.45 | 3.5 | 13.4 | |
| II | Ohara PBH6W | 1.8052 | 25.4 | $R_2$ = 12.45<br>$R_3$ = 36.00 | 1.5 | 13.4 | |
| Prism A | BAK4<br>LAK10 | 1.5688<br>1.7200 | 56.13<br>50.41 | | | | $S_1$ = 21.23<br>$S_2$ = 3.41<br>$S_3$ = 2.33 |
| Prism B | BAK4<br>LAK10 | 1.5688<br>1.7200 | 56.13<br>50.41 | | | | $S_4$ = .5<br>$S_5$ = 22.8 |
| III | Ohara S-TIL2 | 1.541 | 47.2 | $R_4$ = PLANO<br>$R_5$ = 12.61 | 3.0 | 12.0 | |
| IV | Ohara PBH71 | 1.923 | 21.3 | $R_5$ = 12.61<br>$R_6$ = 12.61 | 1.5 | 15.4 | |
| V | SCHOTT BK7 | 1.5168 | 64.2 | $R_7$ = 10.06<br>$R_6$ = 12.61 | 7.1 | 15.4 | |
| VI | SCHOTT S-LAM2 | 1.744 | 44.8 | $R_8$ = 25.11<br>$R_9$ = 25.11 | 4.7 | 17.5 | |

TABLE XXIV 4.8X
(24" WD)

| Element | Glass | nd | vd | Radius | Thickness | Diameter | Sep. |
|---|---|---|---|---|---|---|---|
| I | Ohara BAH 27 | 1.7015 | 41.2 | $R_1 = 42.19$<br>$R_2 = 12.45$ | 3.5 | 13.4 | |
| II | Ohara PBH6W | 1.8052 | 25.4 | $R_2 = 12.45$<br>$R_3 = 36.00$ | 1.5 | 13.4 | |
| Prism A | BAK4<br>LAK10 | 1.5688<br>1.7200 | 56.13<br>50.41 | | | | $S_1 = 18.22$<br>$S_2 = 3.41$<br>$S_3 = 2.33$ |
| Prism B | BAK4<br>LAK10 | 1.5688<br>1.7200 | 56.13<br>50.41 | | | | $S_4 = .5$<br>$S_5 = 22.8$ |
| III | Ohara S-TIL2 | 1.5410 | 47.2 | $R_4 = $ PLANO<br>$R_5 = 12.61$ | 3.0 | 12.0 | |
| IV | Ohara PBH71 | 1.923 | 21.3 | $R_5 = 12.61$<br>$R_6 = 12.61$ | 1.5 | 15.4 | |
| V | SCHOTT BK7 | 1.5168 | 64.2 | $R_7 = 10.06$<br>$R_6 = 12.61$ | 7.1 | 15.4 | |
| VI | SCHOTT S-LAM2 | 1.744 | 44.8 | $R_8 = 25.11$<br>$R_9 = 25.11$ | 4.7 | 17.5 | |

The invention described in the above detailed description is not intended to be limited to the specific form set forth herein, but, on the contrary, is intended to cover such alternatives, modifications and equivalents as can reasonably be included within the spirit and scope of the appended claims.

What is claimed is:

1. A magnification loupe carried by spectacles having a pair of lenses comprising:

an eyepiece lens housing having at least one eyepiece lens mounted therein, said eyepiece lens housing being smaller than a lens of said spectacles and including threads thereon;

an objective lens housing having at least one objective lens mounted therein and including a pin aperture and a pin received in said pin aperture engaging said threads such that said objective lens housing is rotatably adjustable relative to said eyepiece lens housing to enable a distance between said eyepiece lens housing and said objective lens housing to be varied.

2. A magnification loupe according to claims, wherein said objective lens housing is removable to permit substitution by a second objective lens housing carrying an objective lens of different magnification.

3. A magnification loupe carried by spectacles having a pair of lenses comprising:

an eyepiece lens housing having at least one eyepiece lens mounted therein, said eyepiece lens housing being smaller than a lens of said spectacles and including threads thereon;

an objective lens housing having at least one objective lens mounted therein and including a pin aperture; and adjustable means for moving said objective lens housing relative to said eyepiece lens housing to vary a distance between said objective lens housing and said eyepiece lens housing;

an optic element disposed on said loupe for increasing a light path length between said at least one objective lens and said at least one eyepiece lens;

wherein said adjustable means includes a pin aperture in said objective lens housing, threads on said eyepiece lens housing opposing said pin aperture, and a pin received in said pin aperture for engaging said threads.

4. A magnification loupe carried by spectacles having a pair of lenses comprising:

an eyepiece lens housing having at least one eyepiece lens mounted therein, said eyepiece lens housing being smaller than a lens of said spectacles and including threads thereon;

an objective lens housing having at least one objective lens mounted therein and including a pin aperture; and adjustable means for moving said objective lens housing relative to said eyepiece lens housing to vary a distance between said objective lens housing and said eyepiece lens housing;

an optic element disposed on said loupe for increasing a light path length between said at least one objective lens and said at least one eyepiece lens, wherein said optic element is a roof-penchan prism; and wherein said adjustable means includes a pin aperture in said objective lens housing, threads on said eyepiece lens housing opposing said pin aperture, and a pin received in said pin aperture for engaging said threads.

5. A magnification loupe carried by spectacles having a pair of lenses comprising:

an eyepiece lens housing having at least one eyepiece lens mounted therein, said eyepiece lens housing being smaller than a lens of said spectacles and including threads thereon;

an objective lens housing having at least one objective lens mounted therein and including a pin aperture; and adjustable means for moving said objective lens housing relative to said eyepiece lens housing to vary a distance between said objective lens housing and said eyepiece lens housing;

an optic element disposed on said loupe for increasing a light path length between said at least one objective lens and said at least one eyepiece lens wherein the optic element is a roof-penchan prism that includes two prisms separated by a spacer having an aperture centered on an optical axis of said loop; and wherein said adjustable means includes a pin aperture in said objective lens housing, threads on the surface of said eyepiece lens housing opposing said pin aperture, and a pin received in said pin aperture for engaging said threads.

* * * * *

UNITED STATES PATENT AND TRADEMARK OFFICE
CERTIFICATE OF CORRECTION

PATENT NO.   : 6,201,640 B1                                Page 1 of 1
DATED        : March 13, 2001
INVENTOR(S)  : Caplan, et al.

It is certified that error appears in the above-identified patent and that said Letters Patent is hereby corrected as shown below:

<u>Column 25,</u>
Line 44, please delete the word "claims" and insert therefor -- Claim 1 --.

Signed and Sealed this

Sixth Day of November, 2001

*Attest:*

*Attesting Officer*

NICHOLAS P. GODICI
*Acting Director of the United States Patent and Trademark Office*